US010821165B2

(12) United States Patent
Mahu et al.

(10) Patent No.: US 10,821,165 B2
(45) Date of Patent: Nov. 3, 2020

(54) VACCINE STRAINS OF BRACHYSPIRA HYODYSENTERIAE

(71) Applicant: UNIVERSITEIT GENT, Ghent (BE)

(72) Inventors: Maxime Mahu, Sinaai (BE); Frank Pasmans, Sint-Pieters-Kapelle (BE); Filip Boyen, Merelbeke (BE); An Martel, Sint-Pieters-Kapelle (BE); Freddy Haesebrouck, Merelbeke (BE); Sven Arnouts, Bertem (BE)

(73) Assignee: Universiteit Gent, Ghent (BE)

( * ) Notice: Subject to any disclaimer, the term of this patent is extended or adjusted under 35 U.S.C. 154(b) by 70 days.

(21) Appl. No.: 16/068,409

(22) PCT Filed: Dec. 22, 2016

(86) PCT No.: PCT/EP2016/082386
§ 371 (c)(1),
(2) Date: Jul. 6, 2018

(87) PCT Pub. No.: WO2017/118581
PCT Pub. Date: Jul. 13, 2017

(65) Prior Publication Data
US 2019/0015495 A1 Jan. 17, 2019

(30) Foreign Application Priority Data

Jan. 7, 2016 (EP) .................................. 16150392
May 19, 2016 (EP) .................................. 16170374

(51) Int. Cl.
*A61K 39/02* (2006.01)
*C07K 14/20* (2006.01)
(Continued)

(52) U.S. Cl.
CPC .......... *A61K 39/0225* (2013.01); *C07K 14/20* (2013.01); *C12Q 1/689* (2013.01);
(Continued)

(58) Field of Classification Search
CPC .......... A61K 2039/52; A61K 2039/542; A61K 39/0225; A61K 2039/552; A61K 2039/54; C07K 14/20; C12Q 1/689
See application file for complete search history.

(56) References Cited

U.S. PATENT DOCUMENTS 5,882,655 A    3/1999 ter Huurne et al.

FOREIGN PATENT DOCUMENTS

CN    103789327 A    5/2014
WO    WO98/20899 A1   5/1998
(Continued)

OTHER PUBLICATIONS

Matthew Bellgard et al: "Genome Sequence of the Pathogenic Intestinal Spirochete Brachyspira hyodysenteriae Reveals Adaptations to Its Lifestyle in the Porcine Large Intestine", PLOS One, Public Library of Science, US vol. 4, No. 3 Mar. 1, 2009 (Mar. 1, 2009), pp. e4641,1-e4641.12. (Year: 2009).*
(Continued)

*Primary Examiner* — Jana A Hines
(74) *Attorney, Agent, or Firm* — Dinsmore & Shohl, LLP

(57) ABSTRACT

The present invention relates to *Brachyspira hyodysenteriae* strains and their use in diagnosis or treatment. In addition, the invention provides a vaccine against diarrheal disease, in particular swine dysentery.

3 Claims, 11 Drawing Sheets

Specification includes a Sequence Listing.

(51) Int. Cl.
C12Q 1/689 (2018.01)
A61K 39/00 (2006.01)
(52) U.S. Cl.
CPC ...... A61K 2039/52 (2013.01); A61K 2039/54 (2013.01); A61K 2039/542 (2013.01); A61K 2039/552 (2013.01)

(56) References Cited

FOREIGN PATENT DOCUMENTS

| WO | WO2010054437 A1 | 5/2010 |
| WO | WO2013010260 A1 | 1/2013 |

OTHER PUBLICATIONS

La et al., "Evidence that the 36 kb plasmid of Brachyspira hyodysenteriae contributes to virulence", Veterinary Microbiology, 53, 2011, pp. 150-155.
La et al., "Absence of a set of plasmid-encoded genes is predictive of reduced pathogenic potential in Brachyspira hyodysenteriae", Veterinary Research, 45:131, 2014, pp. 1-7.
La et al., "Protection of pigs from swine dysentery by vaccination with recombinant BmpB, a 29.7 kDa outer-membrane ipoprotein of Brachyspira Hyodysenteriae", veterinary microbiology, 102(1-2), 2004, pp. 97-109.
Diego et al., "Serpulina Hyodysenteriae challenge of fattening pigs vaccinated with an adjuvanted bivalent bacterin against swine dysentery", Vaccine, vol. 13, No. 7, 1995, pp. 663-667.
Bellgard et al., "Genome Sequence of the Pathogenic Intestinal Spriochete Brachyspira Hyodysenteriae Reveals Adaptations to Its Lifestyle in the Procine Large Intestine", PloS one, vol. 4, Issue 3, 2009, pp. 1-12.
Barth et al., "Demonstration of genes encoding virulence and virulence life-style factors in *Brachyspira* spp. isolates from pigs", Veterinary Microbiology, 155, 2012, pp. 438-443.
Hyatt et al., "Reduced Virulence of Serpulina hyodysenteriae Hemolysin-Negative Mutants in Pigs and Their Potential to Protect Pigs against Challenge with a Virulent Strain", Infection and Immunity, 62(6), 1994, pp. 2244-2248.
Hudson et al., "Swine dysentery: protection of pigs by oral and parenteral immunisation with attenuated Treponema hyodysenteriae", Research in Veterinary Science, vol. 21, No. 3, 1976, pp. 366-367.
Lysons et al., "An Avirulent Strain of Treponema Hyodysenteriae Isolated from Herds Free of Swine Dysentery", In Proceedings of the 7th International Pig Veterinary Society Congress 1982, Mexico City, Mexico: The Society, p. 40.
Olson et al., "Exacerbated onset of dysentery in swine vaccinated with inactivated adjuvanted Serpulina hyodysenteriae", Am J Vet Res, vol. 55, No. 1, 1994, pp. 67-71.
Black et al., "Analysis of Multiple Brachyspira Hyodysenteriae Genomes Confirms that the Species Is Relatively Conserved but has Potentially Important Strain Variation", PLoS One, 22;10(6), 2015, pp. 1-16.
Achacha et al., "Development of an Experimental Model Allowing Discrimination Between Virulent and Avirulent Isolates of Serpulina (Treponema) hyodysenteriae", Can J Vet Res, vol. 60, 1996, pp. 45-49.
Davis et al, "The Brachyspira Hyodysenteriae ftnA Gene: DNA Vaccination and Real-Time PCR Quantification of Bacteria in a Mouse Model of Disease", Current Microbiology, vol. 50, 2005, pp. 285-291.
Gabe et al., "Isolation of Extracytoplasmic Proteins from Serpulina hyodysenteriae B204 and Molecular Cloning of the flaB1 Gene Encoding a 38-Kilodalton Flagellar Protein", Infection and Immunity, vol. 63, No. 1, 1995, pp. 142-148.
Holden et al., "An evaluation of the immunogenicity and protective responses to Brachyspira hyodysenteriae recombinant SmpB vaccination", Veterinary Microbiology 128, 2008, pp. 354-363.
Johansson et al., "Identification of three clusters of canine intestinal spirochaetes by biochemical and 1 6S rDNA sequence analysis", Journal of Medical Microbiology, vol. 53, 2004, pp. 345-350.
Muir et al., "Cloning and Expression of a Serpula (Treponema) hyodyseneriae Hemolysin Gene", Infection and Immunity, vol. 60, No. 2, 1992, pp. 529-535.
Peppler, "Isolation and Characterization of Isogenic Pairs of Domed Hemolytic and Flat Nonhemolytic Colony Types of Bordetella pertussis", Infection and Immunity, vol. 35, No. 3, 1982, pp. 840-851.
Waters et al., "Systemic and mucosal immune responses of pigs to parenteral immunization with a pepsin-digested Serpulina hyodysenteriae bacterin", Veterinary Immunology and Immunopathology, vol. 69, No. 1, 1999, pp. 75-87.
Weissenbock et al., "Amplification and sequencing of *Brachyspira* spp. specific portions of nox using paraffin-embedded tissue samples from clinical colitis in Austrian pigs shows frequent solitary presence of Brachyspira murdochii", Veterinary Microbiology, vol. 111, 2005, pp. 67-75.
Rubin et al., "Reproduciton of Mucohaemorrhagic Diarrhea and Colitis Indistinguishable from Swine Dysentery following Experimental Inoculation with "Brachyspira hampsonii" Strain 30446", PLoS One, vol. 8, Issue 2, e57146, 2013, pp. 1-14.
Mirajkar et al., "Molecular Epidemiology of Novel Pathogen "Brachyspira hampsonii" Reveals Relationships between Diverse Genetic Groups, Regions, Host Species, and Other Pathogenic and Commensal *Brachyspira* Species", Journal of Clincial Microbiology, vol. 53, No. 9, 2015, pp. 2908-2918.
XP-002756271 UniProt, Sep. 16, 2015, retrieved from EBI accession No. Uniprot:A0A0HOWAF2, p. 1.
International Search Report and Written Opinion, completed Mar. 2, 2017, pertaining to International Application No. PCT/EP2016/082386 filed Dec. 22, 2016.
European Search Report, completed Apr. 11, 2016, pertaining to Application No. EP16150392.5 filed Jan. 7, 2016.

* cited by examiner

BHWA1_RS02885 (hemolysin activation protein)

ATGCGTTTAGTAAGAGAAAAAAAATAAAAGAAGAGGATAAAAAGTATTGGGAAAAATCAAGTTCT
ATGATACCTACCCTATTAGTTGGCAATAACATAGTAAATATATCTGCGAGTTCTATTATAACAGTATTT
GCAGTAAGGCTTGCTGATATTCTGCCGCATGTATCAACAAATATAATGGTTACAATATCAACTGCTAC
AATAACAATACTTATTATTATATTTGGTGAAATACTGCCAAAAGTCTTAATGAGAGTAAATGCTGAAA
AAGTAATGCCTTATCTTTTATACTTTATGAAATTTTGCCATTTTATATTCAAGCCTATAACCTTTTAAT
GGATAAAGTAACTACTTTTATAATGAATTATTTCGTTCCTAAAAGATTAAGAGATGCTGAAAAAGAA
GTGCATTATCAAGTATGGACGATATAACAACAATAATACATTTGGGGCATAAAGAAGGTATAATAAA
AGAATATACACATGAAATGCTTACAGGTGTAATAGATTTCAGAAATAAAACTGTAGAAGAAATAATG
ACTCCTCGTGTTGATATGGTATGTATTGAGGCTGAAACTGATGTAAATGAAATAATAAAACTTACTGT
AGAAACAGGGCTTTCAAGATTTCCGGTTTATGAGGAAACTGTTGATCATATAATAGGAATTTTCCATA
CTAGAGCTTTATTTAAAGAGTATGTTAAAGGCGGCGGAAAAATGAATAAAATAAAAAAGAAAGCAA
TAGATTATATAATGCTTCCCTACTTTGTACCTGAAACTAAAACTATAAGCAGCTTATTTAGTGATATGC
AAAAGAAAAAACTTCAGATGGTAATTACTATTGATGAATACGGCGGAACTGCTGGGCTTGTTACTAT
GGAAGATATAATAGAAGAGATAATGGGTGATATAGAAGATGAAAGTGATAAAAAGAAGCTGATG
TAATAAGATTTAAGGGAAAAAGAATTATAATAAATGGAAATGCTTCTATAGAAGATGTCAACAAAAC
TTTAAAATTAGAATTAGAGCATGAAGAATATCAAACTATAGCAGGATATGTTATTGATATGCTTGATC
ATATACCTGAAACAAATGAGAGATTCATATTAAAAGGATATAGAGTAAGAATAATGAAAGTTGAAG
ACAGAAGAATAGTTGAAATGGAATTTACTCCTATAAAATTTGCAAGAACAAATGAAAGTGATAATAT
TGATATACAAGAGACATCTGATTCAGAAAAAAATGATTTAGAAATTTTAAATGAATAA (SEQ ID NO: 1)

BHWA1_RS02195 (hemolysin III)

ATGGAGAAAAGTGCTTTTTATATAGATATACAAAACAAATCTAATAAATCAAAAAAGATAGGGGAGC
TATACTCAGCAATATCCCATGGCATAGGAGCTTTACTTGGTATTGCTGGACTTGTTCTTATGCTTGTAA
AAATAAAAATGAATCCTATACCTATAATTATTTATGGAGTTGGTATAATCTTTTTATATACATTCAGTT
CTTTATATCATTTCTTTCCTGACGGTAAAATAAAACAAATATTTAGAAAATTTGATCACATAGGAATAT
ATGTGTTTATAGCCGCAACTTATACTCCAGTTTGTATATTTTCACTTCCTAGAAACATAGGAATACCAA
TATTATCAGTAATATGGTCTTGTGCTTTGATAGGTATATTATCTAATACAGTTATAAAATATAAAAATA
TTGTTCTAAGGCTAGTTTATATATATTAATGGGCTGGATAATAATATTTGCATTCAAACCATTAATGA
ATAGATTTGATATTTTGCATTTAAATTGGCTTATATGGGGAGGAATATTTTATACTATAGGTGCTTTCT
TATATGCTTTAGGTAAAAAATGCAATGATAAAACTAAGCAATTCACTCATGATATTTTCCAT (SEQ ID NO: 2)

Figure 4

BHWA1_RS09085 (hemolysin III channel protein)

ATGAATGCTGATTTGAATAATAATATAGTAAAGAATTCTGTTTCTAAGATAAGCGCTGTTATATGCAT
AATATGTGCTAGTTCGGCAATAGCTGTCTTAGTGCTTTTAATAATTAATTCTAAAACTGCAAGGGAAA
TTACTTCATTTTCTCTATACTCAAGTTTTTTAACAATATTTTATATAATAAATTCGATATATCATTTTTTT
CCTTTTAACAATAAAGCAAAAAAAGTTTTTTATATATTATCCCATGCATTTTTTATTATGATGATATGG
GGTATATACATTCCTCCATGCCTAATATCATTACAAAATGGATGGGGATGGAGTTTCTTTGGTATTAT
TACAGGTTTATGTGCATTAGGCATCACATTAAGAAGCGTATTCGGATACAGATGGCGTGGTGCTACA
GAAACTATATATTATTTTCTATTAAATTGGGTTTGGCTTATAGCAATTTCAAAAATATCTACTGCTGTA
GGTGAATATGGAGCAATATTATATTTAACAGGTTTTCTTCTGCTCAATATAGCAATGGTATTTTACAG
ACTCGCTATGTATGAAGCCAATAGAAGATATACTTTATTTTTACCTTTATTTTATTCGCTTTTAATAATA
TCAAATATATGCCATGCAGTATTTATGTTTAGATATGTTGCTAACATTTTCTAA (SEQ ID NO: 3)

tlyA

TATACTGAAACTTTTGAATCAGTTTATATAACTTCAAATATATTAGAAAGCAATCATACTCAAATGCTT
TTAAAAGTAAATATGAGAGATAAAGAAAGAAATTCTCTTTCTATAATAAAATCTTTCCTTGGATTATA
ATACTAATATAAATGCGATTAGATGAATATGTGCATAGTGAATGCTATACAGAAAGCAGATCTAAAG
CACAGGATATAATACTAGCCGGTTGTGTTTTTGTTAATGGAGTAAAGGTAACTTCTAAGGCTCATAAA
ATAAAAGATACTGATAATATAGAAGTTGTTCAGAATATAAAATATGTATCAAGAGCTGGAGAAAAAT
TAGAAAAGGCGTTTGTAGAATTTGGAATATCTGTAGAAAATAAAATATGTTTAGATATAGGAGCTTC
TACAGGAGGATTTACAGATTGTCTGCTTAAGCATGGTGCTAAAAAAGTTTATGCTCTTGATGTAGGA
CATAATCAGCTAGTTTATAAACTTCGTAATGATAATAGGGTAGTGTCAATAGAAGATTTCAATGCCAA
AGATATAAATAAGAAATGTTCAATGATGAAATCCATCTGTAATAGTAAGTGACGTATCATTTATAT
CAATAACAAAAATAGCACCAATCATATTTAAAGAATTAAATAATTTAGAGTTTTGGGTAACTTTAATA
AAACCACAATTTGAAGCTGAAAGAGGTGATGTTTCAAAAGGCGGTATAATACGAGATGATATACTTA
GAGAAAAATATTAAATAATGCTATTTCAAAGATAATAGACTGCGGATTTAAAGAAGTTAATAGAAC
CATCTCTCCTATAAAAGGTGCTAAAGGTAATATAGAATATTTAGCTCATTTTATTATTTAATCATTTTCT
ATTTTATGTGTATTTCTCTGTTTATATATTTCATATTCTTTATA (SEQ ID NO: 4)

Figure 4 - continued tlyB

TAATAAGGACAATTCTCATAAGACTAATACTGCATCATCTAGTAAGACTAACATAAATGTTGTTAATGTAGCTA
ATAGTAGTTTTATTTAAAATTTAAAACCTATAATAGAAATTCTAAATTATACATTAGCATTCCTTTATGTTAATGT
ATAATTTTGTTTTATTTATAATAGTATTTCTATTATATCCGATAATGATTATTAAAATATTTTATATACGTAAAATA
TAATACAGGATTATAATATGTTTCAATTTCATTTAACAAGCAAAGCAAAAAAGGTAATAGAATTATATGCTCAG
GAAGAAGCAAAAAGATTAAATCATGATATGGTTACACCTGAACATATACTTTTGGGGCTTCTTCATGAATCAGA
GGCTTTGGCAACACGTGTTTTGATGAGATTGAAAATTGATTTGGACAGACTTAAATTAGAATTAGAATCAGCTA
TGGTAAAATCTTCAACTACAAAAGTATTTGGAACTTTACCTACAGCTCCAAGAGTACAGAAACTTATAAGCAGA
TCTGCTGAAGAGGCTAGGGCTTTAAGTCATAACTATATAGGTACTGAACATTTACTTCTTGGACTTCTAAGAGA
AGAAAGTGGTACAGCTTATAATGTACTTACAAGTATGGGGCTTGAGCTTACTATATTAAGACAAGAAATATTA
AAAATGCTTGGTGTTGCTGGAAGTAATATTTCTTCTATGGAACAGACAAGTCAGGAAGATAATGTAAAAAAGG
TAAAAACACCTACTTTAGATCAATTTGCCAGAGATTTAACTAAAATGGCTAGAGACAAGGCTTTAGACAGAGTT
ATAGGCAGAGAAAATGAAGTAATGAGAGTTGTTCAGATTTTATCAAGAAGAAAGAAAAATAATCCTATACTTC
TTGGTGAGCCTGGTGTAGGTAAAACAGCTATAGTAGAGGGACTTGCTGAAAAGATAGTAGCTGCTGATGTAC
CTGATATACTTCTAAAAAAACGTGTATTAACTTTAGATTTGTCTTCAGTTGTTGCTGGTACAAAATACAGAGGTG
AATTTGAAGAGAGAATAAAAAACATAGTTTTAGAAATAAAAAAAGCTAGTAATATTATTATATTCATAGATGA
GCTTCATACATTAATAGGGGCAGGTGGTGCTGAAGGTGCTTTAGATGCTGCTAATATGTTAAAGCCGGCACTT
TCAAGAGGCGAGATTCAATGTATAGGTGCCACTACTATAAATGAATATAAAAAATATATAGAAAAAGACGGTG
CTTTGGTTAGAAGATTCCAGCCTATAAATGTTGAAGAGCCTAGTATAGAGGATACTATTGAAATATTGAATGGT
ATCAAAGGTAAATATGAAGAACATCATAAAGTAAAATATACTGATGAAGCAATAAATGCTGCTACTGTATTGA
GTAAGAGATATATTTTTGAAAGACATTTGCCTGATAAAGCTATAGACTTAATAGATGAGGCAGGTTCAAGAGC
AAGACTTCTTAATATGACAAGACCTCAGGAGTTTAAAGATTTAGAAAAGAAAATAGAAGAGCTTAATCAGCAA
AAGAAAAGAGTTGTTGAGAGTCAGAATTTCGAAGATGCTGCTAAAATAAGAGATGAAATTACTTCTTTACAGG
AAGAGCTTTCTAAAAAAGAAGAAAAATGGCGTGAAGAAAGAGAAAAGATAGAAACATTTATTGAAGAAGATG
ATATAAGACATGTTATATCAGAAATAACTAATATACCTATAAAAAGATTATTAAACTCAGAAAGTAAAAGACTT
ATAGGTATGGAAGAAGAATTGCATCAGAAAGTCGTAGGACAGAAAGAAGCTATATCTTCTATATCTAAGGCTA
TAAGAAGAAGCAGAGCAGGACTTAAAACATCAAAAAGACCTCTTGGAAGTTTTATTTTCCTGGGACCTACAGG
TGTTGGTAAAACTGCTTTAGCTAAAGTTCTTTCAGAGTTTATGTTTGGAGACAGCGATGCTCTTATCAGAATAG
ATATGAGTGAGTTTATGGAAAAGTTTGCGGTAAGCAGACTTATAGGAGCTCCTCCTGGATATGTTGGTTATGA
AGAGGGAGGCGGACTTACTGAAAAGGTGAGAAGAAAGCCTTATTCTCTTATACTTTTTGATGAAATAGAAAAA
GCTCATCCTGATGTTACTAATATACTTTTACAAGTACTTGAAGAAGGACAGCTTACTGATAATTTTGGAAGAAA
AGTTGATTTTTCAAATACTATTATAATAATAACAAGTAACTTAGGTGCAAGAGATATTGTAAAAGGAAGTTCTT
TAGGATTTAATGCTGTTGGAAGCGAAAAAGATGCTAATGATATTAAAAATTTTGCTTTAGAAGAATTAAAACA
GAATTTTAATCCTGAGTTTTTAAATAGAATTGATGATATCATAGTATTCCATACTTTAAGTAAAGAGGATTTGAA
AGATATTATTAATATAATGCTTAAAGAGCTTAATGAAGCTATTAAAGAAAGAAATATTGTTATTAATTTAAGCG
AAGAAGCTAAGAATTATATCATAGATAAAGGATTCGATAAGAAGTATGGTGCTAGAAGTTTAAGAAGGGCTAT
ACAGAAAGAGATAGAGGATTATGTGAGTACCGAAATATTATTCGGTAATATTGAAGATGGTGATACTATTAAC
GTTGATGCTAATGATGGCTCTTTGATATTTTCTTATGATAAGTCAGTTAAGACTGAGAATAAGGAATTATCTAA
AAGTTAG (SEQ ID NO: 5)

Figure 4 - continued tlyC

TAAAAGGGATACATCATAATTATACTAGAAAATCATTAATGGAAAATAATAAGAAAATGAAGGAATT
ATACAAAAAAGTGATAAAAACAATAAAAGAAAATAAATCATAATTTAAGGATATATATAAAATGCCA
ATAAAAAAATTAATATCTAAGATAGTGAAAAAAAAAGATAGTGATACTGAAAAAAATAATTATATAA
ATTTATCCGCATTAACAGAAGCAGAAAGAGAAATTATAACTAATACTATAGAATTGAAATCAAAGAG
CGTAAGAGAAATAATGGTGCCTAGGGTTGATGTTGTTATGATACCTATGGAATCTTCTTATGATAAG
GTTATAAAGGCTTTTAATAGAGATAGAAATTCCAGAATTCCTGTATACAAAGACGGCATAGATGATA
TAGTAGGGGTTTTGTATGTAAAAGATTTGATTGATGCAGAAGAAAAAATTTCTCACTTAAAAAAATT
CTACATAAACCTTTATTCGTACCAATATCAATTTCATTAATGGAATTATTAAAAAATTTCAGAGAAAAG
CAAATTCATATTGCTATGGTTGTTGATGAATATGGCGGATTTTCTGGTATTGTTTCTATGGAAGATGT
GCTTGAGCAGATTATAGGTGATATTAGAGATGAATACGATGAAGAAGACGAAGAAATAAAGAGCAA
TGATGATGGAACATATTTAGTTGATGCAAGAACTAGAATAGATGATTTTAATAAATATGAGATACTTC
CGCCTATACCGGATGATGAGGCAGATACAGTTGGAGGATTTTTATTTTCATACTTGGGCAGGCTTCCT
AAAAGAAATGAGGATATAGAATATAATGGATATTCATTTACTGTAGTTGGTAAAAGCGGAAATATTG
TTACTAAAATAAGAATAGAAAAATTAAAAAAAGATAATACAGCAAAAAATAAAGATTA (SEQ ID NO: 6)

hlyA

CGGTTGACGGCGGAATGTCAATGTAATTATAAAAAGTATATAATGTGTTTAAAAACACTTTATTAAT
AAACAATATACAATTTAAGGAGAATTAAAAATGGCATTAATCGATGAAATTAAAGATGTTGTTGCTA
ATCAATTAAACATCTCAGACAAAAGTAAAATCACTGATACAGCTTCTTTCGTAGATGATTTAAACGCT
GATTCACTTGATTTAGTAGAATTAATCATGGAATTAGAAAAACGTTATGAAATCAAAATTCCTCAAGA
AGATCAAGAAAAATCAAAATGTAGCTGATGCTGCTAAATACATTGAAGAACATAAAAAATAATTA
TACTATTTAAATTTCCCGTAAATAGAATTATGTCTTTTACGGGAAATTTTTCGATATAGTTCAAAATCA
TAGGAGTTTTATATATGAGTGAACGTAGAGTTGTAATTACGGGGCTTGGAATAGTAAGTTC (SEQ ID NO: 7)

Figure 4 - continued

NADH oxidase (nox)

CTATGCTAGTCCTGAAAGTTTGAGAGGTGAAGGCATCGATGTTTATATGGGACATGATGTTACTAAA
ATAGACTGGGCTAACAAAAAATTATGTGTAAAAGAACTAAAAACAGGAAAAGAGTTTGAAGACACT
TACGATAAACTTATTCTTGCTACTGGTTCTTGGCCTGTAACTCCTCCTATCGAAGGCTTAAAACAAGAA
GGAACTACTTACGGACTTAAAAAAGGTATTTTCTTCTCTAAGCTTTATCAGCAAGGACAAGAAATTAT
TGATGAAATAGCTAAACCAGATGTTAAAAAAGTTATGGTAGTTGGTGCTGGATACATAGGTGTTGAA
CTTATAGAAGCATTCAAAAACCATGGTAAAGAAGTTATCTTAATGGAAGCTATGCCTAGAGTTATGG
CTAACTACTTTGATAAAGAAATCACTGATGAAGCTGAAAAAGAATCAAAGAAGCTGGCATAGAAAT
GCATTTAGGTGAAACTGTTAAGAAATTTGAAGGTGATGACAGAGTTAAAAAAGTTGTTACTGACAAA
GGTTCTTATGATGTAGATATGGTAGTTATGTCTGTTGGTTTCAGACCTAATAATGAACTTTATAAAGA
TTATTTAGAAACTTTACCTAATGGTGCTATTGTAGTAGATACTACTATGAAAACTACTAAAGATCCTG
ATGTATTTGCTATAGGTGACTGTGCTACTGTATATTCAAGAGCTTCTGAAAAACAAGAATATATTGCT
TTAGCTACTAATGCTGTAAGAATGGGTATTGTTGCTGCTAATAATGCTTTAGGAAAACATGTTGAATA
TTGCGGTACTCAAGGTTCTAATGCTATTTGTGTATTTGGATACAATATGGCTTCTACTGGTTGGTCTG
AAGAAACTGCTAAGAAAAAGGATTAAAAGTAAAATCTAACTTCTTCAAAGATTCTGAAAGACCAGA
ATTTATGCCTACTAATGAAGATGTTTTAGTAAAAATCATTTATGAAGAAGGCAGCAGACG (SEQ ID NO: 8)

16S rRNA

CGCATATACTCTTGCTACATAAGTAGAGTAGAGGAAAGGAGCAATCCGCTTTACGATGAGCCTGCGG
CCTATTAGCCTGTTGGTGGGGTAACGGCCTACCAAAGCTACGATAGGTAGCCGACCTGAGAGGGTG
ACCGGCCACATTGGGACTGAGATACGGCCCAGACTCCTACGGGAGGCAGCAGCTGAGAATCTTCCA
CAATGGACGAAAGTCTGATGGAGCGACATCGCGTGAGGGATGAAGGCCTTCGGGTTGTAAACCTCG
GAAATTATCGAAGAATGAGTGACAGTAGATAATGTAAGCCTCGGCTAACTACGTGCCAGCAGCCGC
GGTAATACGTAGGAGGCAAACGTTGCTCGGATTTACTGGGCGTAAAGGGTGAGTAGGCGGACTTAT
AAGTCTAAGGTGAAAGACCGAAGCTCAACTTCGGAAACGCCTCGGATACTGTAAGTCTTGGATATTG
TAGGGGATGATGGAATTCTCGGTGTAGCGGTGGAATGCGCAGATATCGAGAGGAACACCTATAGCG
AAGGCAGTCATCTGGGCATTTATCGACGCTGAATCACGAAAGCTAGGGGAGCAAACAGGCTTAGAT
ACCCTGGTAGTCCTAGCCGTAAACGTTGTACACTAGGTGCTTCTATTTAAATAGGAGTGCCGTAGCTA
ACGTCTTAAGTGTACCGCCTGAGGAGTATGCCCGCAAGGGTGAAACTCAAAGAAATTGACGGGTCC
CCGCACAAGTGGTGGAGCATGTGGTTTAATTCGATGATACGCGAAAAACCTTACCTGGGTTTGAATT
GTAAGATGAATGATTTAGAGATAAGTCAGACCGCAAGGACGTTTTACATAGGTGCTGCATGGCTGTC
GTCAGCTCGTGTCGTGAGATGTTGGGTTAAGTCCCGCAACGAGCGCAACCCTCACCCTTTGTTGCTAC
CGAGTAATGTCGGGCACTCTTAGGGGACTGCCTACGTTCAAGTAGGAGGAAGGTGGGGATGATGTC
AAGTCCTCATGGCCCTTATGTCCAGGGCTACACACGTGCTACAATGGCAAGTACAAAGAGAAGCAAG
ACCGCGAGGTGGAGCAAAACTCAAAAAAGTTGCCTCAGTTCGGATTGGAGTCTGAAACTCGACTCCA
TGAAGTTGGAATCACTAGTAATCGTAGATCAGAACGCTACGGTGAATACG (SEQ ID NO: 9)

Figure 4 - continued

BHWA1_RS02885 (hemolysin activation protein)

MRLVREKKIKEEDKKYWEKSSSMIPTLLVGNNIVNISASSIITVFAVRLADILPHVSTNIMVTISTATITILIIIFG
EILPKVLMRVNAEKVMPYLLYFMKFCHFIFKPITFLMDKVTTFIMNYFVPKRLRDAEKRSALSSMDDITTIIH
LGHKEGIIKEYTHEMLTGVIDFRNKTVEEIMTPRVDMVCIEAETDVNEIIKLTVETGLSRFPVYEETVDHIIGI
FHTRALFKEYVKGGGKMNKIKKKAIDYIMLPYFVPETKTISSLFSDMQKKKLQMVITIDEYGGTAGLVTME
DIIEEIMGDIEDESDKKEADVIRFKGKRIIINGNASIEDVNKTLKLELEHEEYQTIAGYVIDMLDHIPETNERFI
LKGYRVRIMKVEDRRIVEMEFTPIKFARTNESDNIDIQETSDSEKNDLEILNE (SEQ ID NO: 10)

BHWA1_RS02195 (hemolysin III)

MEKSAFYIDIQNKSNKSKKIGELYSAISHGIGALLGIAGLVLMLVKIKMNPIPIIIYGVGIIFLYTFSSLYHFFPD
GKIKQIFRKFDHIGIYVFIAATYTPVCIFSLPRNIGIPILSVIWSCALIGILSNTVIKYKNIVLRLVLYILMGWIIIFA
FKPLMNRFDILHLNWLIWGGIFYTIGAFLYALGKKCNDKTKQFTHDIFHIFVLMGSFCHYWFLYSYVIN
(SEQ ID NO: 11)

BHWA1_RS09085 (hemolysin III channel protein)

MNADLNNNIVKNSVSKISAVICIICASSAIAVLVLLIINSKTAREITSFSLYSSFLTIFYIINSIYHFFPFNNKAKKV
FYILSHAFFIMMIWGIYIPPCLISLQNGWGWSFFGIITGLCALGITLRSVFGYRWRGATETIYYFLLNWVWLI
AISKISTAVGEYGAILYLTGFLLLNIAMVFYRLAMYEANRRYTLFLPLFYSLLIISNICHAVFMFRYVANIF
(SEQ ID NO: 12)

TlyA

MRLDEYVHSECYTESRSKAQDIILAGCVFVNGVKVTSKAHKIKDTDNIEVVQNIKYVSRAGEKLEKAFVEFG
ISVENKICLDIGASTGGFTDCLLKHGAKKVYALDVGHNQLVYKLRNDNRVVSIEDFNAKDINKEMFNDEIP
SVIVSDVSFISITKIAPIIFKELNNLEFWVTLIKPQFEAERGDVSKGGIIRDDILREKILNNAISKIIDCGFKEVNR
TISPIKGAKGNIEYLAHFII (SEQ ID NO: 13)

Figure 4 - continued

TlyB

MFQFHLTSKAKKVIELYAQEEAKRLNHDMVTPEHILLGLLHESEALATRVLMRLKIDLDRLKLELESAMVKS
STTKVFGTLPTAPRVQKLISRSAEEARALSHNYIGTEHLLLGLLREESGTAYNVLTSMGLELTILRQEILKMLG
VAGSNISSMEQTSQEDNVKKVKTPTLDQFARDLTKMARDKALDRVIGRENEVMRVVQILSRRKKNNPILL
GEPGVGKTAIVEGLAEKIVAADVPDILLKKRVLTLDLSSVVAGTKYRGEFEERIKNIVLEIKKASNIIIFIDELHT
LIGAGGAEGALDAANMLKPALSRGEIQCIGATTINEYKKYIEKDGALVRRFQPINVEEPSIEDTIEILNGIKGK
YEEHHKVKYTDEAINAATVLSKRYIFERHLPDKAIDLIDEAGSRARLLNMTRPQEFKDLEKKIEELNQQKKR
VVESQNFEDAAKIRDEITSLQEELSKKEEKWREEREKIETFIEEDDIRHVISEITNIPIKRLLNSESKRLIGMEEE
LHQKVVGQKEAISSISKAIRRSRAGLKTSKRPLGSFIFLGPTGVGKTALAKVLSEFMFGDSDALIRIDMSEFM
EKFAVSRLIGAPPGYVGYEEGGGLTEKVRRKPYSLILFDEIEKAHPDVTNILLQVLEEGQLTDNFGRKVDFS
NTIIIITSNLGARDIVKGSSLGFNAVGSEKDANDIKNFALEELKQNFNPEFLNRIDDIIVFHTLSKEDLKDIINI
MLKELNEAIKERNIVINLSEEAKNYIIDKGFDKKYGARSLRRAIQKEIEDYVSTEILFGNIEDGDTINVDANDG
SLIFSYDKSVKTENKELSKS (SEQ ID NO: 14)

TlyC

MPIKKLISKIVKKKDSDTEKNNYINLSALTEAEREIITNTIELKSKSVREIMVPRVDVVMIPMESSYDKVIKAF
NRDRNSRIPVYKDGIDDIVGVLYVKDLIDAEEKNFSLKKILHKPLFVPISISLMELLKNFREKQIHIAMVVDEY
GGFSGIVSMEDVLEQIIGDIRDEYDEEDEEIKSNDDGTYLVDARTRIDDFNKYEILPPIPDDEADTVGGFLFS
YLGRLPKRNEDIEYNGYSFTVVGKSGNIVTKIRIEKLKKDNTAKNKD (SEQ ID NO: 15)

HlyA

MALIDEIKDVVANQLNISDKSKITDTASFVDDLNADSLDLVELIMELEKRYEIKIPQEDQEKIKNVADAAKYI
EEHKK (SEQ ID NO: 16)

NADH oxidase (nox)

YASPESLRGEGIDVYMGHDVTKIDWANKKLCVKELKTGKEFEDTYDKLILATGSWPVTPPIEGLKQEGTTY
GLKKGIFFSKLYQQGQEIIDEIAKPDVKKVMVVGAGYIGVELIEAFKNHGKEVILMEAMPRVMANYFDKEI
TDEAEKRIKEAGIEMHLGETVKKFEGDDRVKKVVTDKGSYDVDMVVMSVGFRPNNELYKDYLETLPNGA
IVVDTTMKTTKDPDVFAIGDCATVYSRASEKQEYIALATNAVRMGIVAANNALGKHVEYCGTQGSNAICV
FGYNMASTGWSEETAKKKGLKVKSNFFKDSERPEFMPTNEDVLVKIIYEEGSRR (SEQ ID NO: 17)

Figure 4 – continued

VACCINE STRAINS OF BRACHYSPIRA HYODYSENTERIAE

SEQUENCE LISTING

This application incorporates by reference the material in the ASCII text file "GHE 0026 PA—Sequence Listing_ST25.txt" of 41,140 bytes created on Jul. 5, 2018, and filed herewith.

FIELD OF THE INVENTION

The present invention relates to *Brachyspira hyodysenteriae* strains and their use in a vaccine against diarrheal disease, in particular swine dysentery.

BACKGROUND OF THE INVENTION

*Brachyspira hyodysenteriae* (*B. hyodysenteriae*; previously *Serpula, Serpulina* or *Treponema hyodysenteriae*) is an anaerobic intestinal spirochaete that infects a number of mammalian and avian species of animal and in some cases causes diarrheal diseases. A well-studied example is swine dysentery (SD), a significant endemic disease of pigs worldwide caused by *B. hyodysenteriae* infection in pigs. SD is a contagious mucohaemorrhagic diarrheal disease, characterised by extensive inflammation and necrosis of the epithelial surface of the large intestine. Economic losses due to SD result mainly from growth retardation, costs of medication and mortality. Where SD is established in a piggery, the disease spectrum can vary from being mild, transient or unapparent, to being severe and even fatal.

Medication strategies in individual piggeries may mask clinical signs and in some piggeries SD may go unnoticed, or may only be suspected. Whether or not obvious SD occurs, *B. hyodysenteriae* may persist in infected pigs, or in other reservoir hosts such as rodents, or in the environment. All these sources pose potential for transmission of *B. hyodysenteriae* to uninfected herds.

A number of methods are employed to control swine dysentery, varying from the prophylactic use of antimicrobial agents, to complete destocking of infected herds and prevention of re-entry of infected carrier pigs. All these options are expensive and, if they are to be fully effective, they require the use of sophisticated diagnostic tests to monitor progress. Currently, detection of swine dysentery in herds with sub-clinical infections, and individual healthy carrier animals, remains a major problem and is hampering implementation of effective control measures. A definitive diagnosis of swine dysentery traditionally has required the isolation and identification of *B. hyodysenteriae* from the feces or mucosa of diseased pigs. Major problems involved include the slow growth and fastidious nutritional requirements of these anaerobic bacteria and confusion due to the presence of morphologically similar spirochaetes in the normal flora of the pig intestine. A significant improvement in the diagnosis of affected pigs was achieved with the development of polymerase chain reaction (PCR) assays for the detection of the *B. hyodysenteriae* from feces. Unfortunately in practical applications the limit of detection of PCRs rendered it unable to detect carrier animals with subclinical infections. As a consequence of these diagnostic problems, there is a clear need to develop a simple and effective diagnostic tool capable of detecting *B. hyodysenteriae* infection, at least at the herd level.

The classical treatment of swine dysentery consists of antimicrobial agents. Since acquired antimicrobial resistance is increasing for *B. hyodysenteriae*, the sole use of antibiotics can result in therapeutic failure. Furthermore the use of antimicrobials is of growing public concern due to the development of antimicrobial resistance. The consumer desires safe pork produced with minimal use of antimicrobial products.

An immunological response is induced following colonization with *B. hyodysenteriae*, and pigs recovered from SD are protected from re-infection. Despite this, attempts to develop vaccines to control swine dysentery had very limited success, either because they have provided inadequate protection on a herd basis, or they have been too costly and difficult to produce to make them commercially viable.

Vaccines based on inactivated *B. hyodysenteriae* were reported to have limited success but the main disadvantage of the inactivated vaccines is that they did not provide protection against different serotypes, in contrast to what happens after recovery of an actual infection (Olson et al., 1994; Diego et al., 1995). Furthermore they are difficult and costly to produce on a large scale.

Several attempts have been made to develop attenuated vaccines for swine dysentery (WO9820899; WO2010054437; U.S. Pat. No. 5,882,655). Most of these vaccines are based on a mutant *B. hyodysenteriae* strain which is defective in one or more virulence factors or hemolysin associated genes. Live attenuated vaccines have the advantage over inactivated vaccines that they mimic the natural infection more closely. As a consequence they provide in general a higher level of protection than their inactivated counterparts. However, in several cases it was shown that the use of avirulent strains as vaccine is no guarantee for obtaining significant protection against infection (Hudson M J. et al., 1974; Lysons R. et al., 1982). Also, clinical signs of disease might be (partially) reduced but the degree of infectivity of the vaccinated animals remains high resulting in an enhanced risk of (re)-infection (Hyatt et al., 1994). In addition, genetically modified organisms require a more extensive registration procedure due to safety issues linked to the genetic mutation.

The use of recombinant subunit vaccines is an alternative, since the products would be well-defined, and relatively easy to produce on a large scale. Examples of recombinant vaccine candidates are a 38-kilodalton flagellar protein flaB1 (Gabe et al., 1995), an outer membrane protein BmpB (La et al., 2004), an smpB protein (Holden et al., 2008) and a ftnA protein (Davis et al., 2005). However, these subunit vaccines, either recombinant proteins combined with adjuvant or DNA vaccines harboring DNA for the recombinant protein, were only reported to reduce the severity of a *B. hyodysenteriae* infection in murine models and could not significantly reduce the number of infected animals or the severity of clinical illness in swine models.

The "gold standard" for the control of diseases caused by *B. hyodysenteriae* would be the use of a vaccine to provide animals with immunity, preventing *B. hyodysenteriae* colonization and/or disease. Currently there are no effective vaccines available for protection against *B. hyodysenteriae*. An efficient vaccine would be an important tool to manage swine dysentery in the future.

SUMMARY OF THE INVENTION

The present invention provides strains of *Brachyspira*, in particular *Brachyspira hyodysenteriae*, that are useful as live and attenuated vaccines for inducing protection against *Brachyspira* infection.

In one embodiment, the invention provides an isolated strain of *Brachyspira hyodysenteriae* (*B. hyodysenteriae*) characterized by the presence of one or more genes, preferably all of the genes, comprising or consisting of the nucleic acid sequence selected from the group consisting of SEQ ID NO:1, SEQ ID NO:2, SEQ ID NO:3, SEQ ID NO: 4, SEQ ID NO: 5, SEQ ID NO: 6, SEQ ID NO: 7, SEQ ID NO: 8 and SEQ ID NO: 9. In particular, the strain comprises one or more, preferably all, of the proteins comprising or consisting of the amino acid sequence selected from the group consisting of SEQ ID NO:10, SEQ ID NO:11, SEQ ID NO: 12, SEQ ID NO: 13, SEQ ID NO: 14, SEQ ID NO: 15, SEQ ID NO: 16, and SEQ ID NO: 17. In a further embodiment, the strain comprises four plasmid based virulence associated genes as provided herein. Even more particular, the strain is deposited on 23 Oct. 2015 at the Belgian Co-ordinated Collections of Micro-Organisms under BCCM Deposit No. LMG P-29184, and the invention also encompasses strains or mutants derived thereof having the same or essentially the same advantageous properties. Furthermore, the strain of the present invention is an attenuated strain, which retains its immunogenic properties but is no longer virulent.

The invention further encompasses the use of the strain in the manufacture of a composition, especially a vaccine composition. Said composition further comprises a pharmaceutically acceptable carrier, excipient and/or diluent.

In one embodiment, the present invention provides the strain or composition as described herein for use as a medicament, more particular for use in the treatment, reducing the risk of, or the prevention of an infection with *B. hyodysenteriae* in a subject, and the related clinical signs of said infection, e.g. (mucohemorrhagic) diarrheal disease.

Typically, the strain or composition is administered orally or parenteral to the subject in a therapeutically effective amount.

The invention further provides a method and kit for immunizing a subject against *B. hyodysenteriae* infection by administering the strain or the composition as described herein to said subject. More in particular, the invention encompasses a method and kit for treating, preventing, inhibiting, or reducing (the risk for) a *B. hyodysenteriae* infection, said method comprising administering to a subject in need thereof, a strain or composition as provided herein.

In a further embodiment, the kit for vaccinating a subject against *B. hyodysenteriae* infection comprises: (a) a vaccine composition comprising at least one vaccine strain according to current invention; and (b) instructions for vaccinating a subject.

The invention further provides a method of identifying a candidate vaccine strain of *B. hyodysenteriae* comprising the steps: (a) obtaining a sample of *B. hyodysenteriae*; and (b) determining the presence or absence of one or more (including all) of the nucleic acid molecules as depicted in SEQ ID NOs:1-6, or a sequence substantially identical thereto, and/or the expression of corresponding mRNA or protein products such as e.g. represented by SEQ ID NOs: 10-15, or a sequence substantially identical thereto, wherein the presence of said nucleic acids or expression of corresponding mRNA or protein, is indicative of a vaccine strain of *B. hyodysenteriae*.

In a further embodiment, the invention provides a method of distinguishing a vaccine strain from a virulent field strain (DIVA principle). In addition, the invention provides a method of diagnosing avirulent *B. hyodysenteriae* colonization in an animal, comprising the steps of: (a) obtaining a sample from said animal; and (b) determining the presence or absence of one or more or all polynucleotide sequences comprising the nucleic acid sequences depicted in SEQ ID NOs:1-6, or a sequence substantially identical thereto, and/or the expression of corresponding mRNA or encoded protein products, such as depicted in SEQ ID NOs: 10-15, or a sequence substantially identical thereto, wherein the presence of said nucleic acids or corresponding mRNA or protein products indicates the presence of avirulent *B. hyodysenteriae* colonization in the animal.

BRIEF DESCRIPTION OF THE FIGURES

FIG. 4: Nucleic acid and deduced amino acid sequence for genes BHWA1_RS02195, BHWA1_RS02885, BHWA1_RS09085, tlyA, tlyB, tlyC, hlyA, NADH oxidase, and 16S rRNA of *B. hyodysenteriae* strain BVF1.

DESCRIPTION OF THE INVENTION

Figure 1:
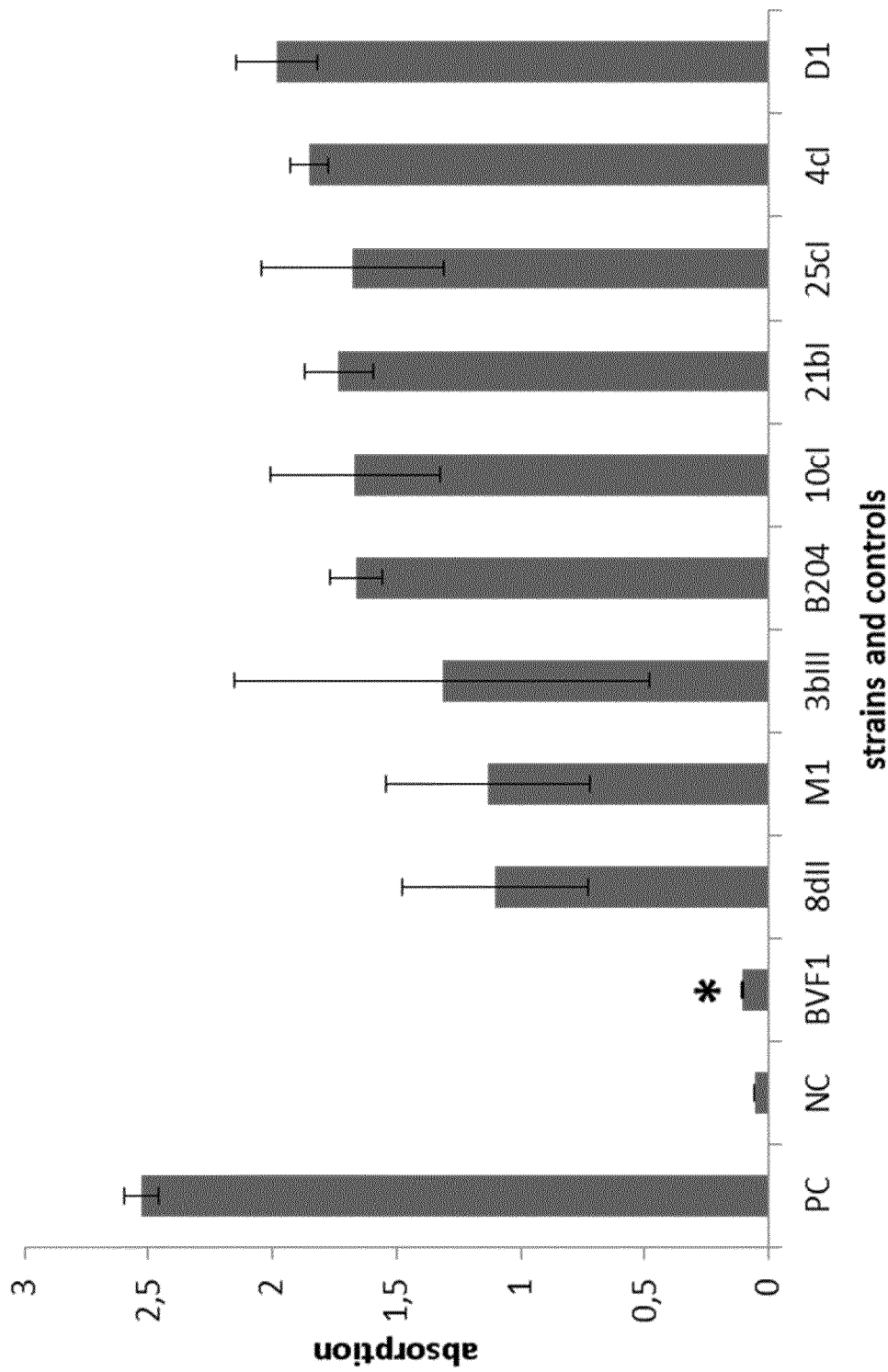
FIG. 1: In vitro hemolytic capacity of different *B. hyodysenteriae* strains. Hemolysis is represented by the mean value of absorption at 450 nm after incubation of red blood cell suspension with supernatant of the different *B. hyodysenteriae* strains. PC: positive control, NC: negative control. Significant differences between *B. hyodysenteriae* strains and reference strain B204 are indicated, *$P<0.01$.

As used herein, the singular forms "a", "an", and "the" include both singular and plural referents unless the context clearly dictates otherwise. The terms "comprising", "comprises" and "comprised of" as used herein are synonymous with "including", "includes" or "containing", "contains", and are inclusive or open-ended and do not exclude additional, non-recited members, elements or method steps. The term "about" as used herein when referring to a measurable value such as a parameter, an amount, a temporal duration, and the like, is meant to encompass variations of +/−10% or less, preferably +1-5% or less, more preferably +/−1% or less of and from the specified value, insofar such variations are appropriate to perform in the disclosed invention. It is to be understood that the value to which the modifier "about" refers is itself also specifically, and preferably, disclosed. Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any >3, >4, >5, >6 or >7 etc. of said members, and up to all said members. All references, and teachings specifically referred to, cited in the present specification are hereby incorporated by reference in their entirety. Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous. Reference throughout this specification to "one embodiment" or "an embodiment" means that a particular feature, structure or characteristic described in connection with the embodiment is included in at least one embodiment of the present invention.

One embodiment of the invention provides an isolated strain of Brachyspira hyodysenteriae (B. hyodysenteriae). B. hyodysenteriae are anaerobic, gram-negative, chemotrophic bacteria belonging to the class Spirochaetae and are characterized by their long, slender, helical shape. Animals infected by B. hyodysenteriae develop diarrheal diseases. Porcine animals infected by B. hyodysenteriae develop swine dysentery (SD) characterized by extensive inflammation and necrosis of the epithelial surface of the large intestine. Accordingly, while it is particularly contemplated that the strains, compositions, kits and methods of the invention are suitable for use in porcine animals (pigs and hogs), they are also applicable to other mammalian and avian species of animal, including humans, companion animals such as dogs and cats, and domestic animals such as chicken and geese, horses, cattle and sheep, or zoo mammals such as non-human primates, felids, canids and bovids. A "subject" as used herein includes a human or animal, in particular porcine animals such as pigs, hogs and piglets.

The present invention relates to a new B. hyodysenteriae strain, and its use. Surprisingly it was seen that by administering the strain to a subject a significant inhibition of colonization and inhibition of fecal shedding was achieved after challenge with a virulent B. hyodysenteriae strain, thereby substantially reducing the chance of (re)-infection. The strain of the invention is safe since no clinical symptoms of diarrhea were noted and no negative effect on growth of the vaccinated subject was observed. The strain not only stimulates active immunity (the ability of the strain to generate in a subject the development of a humoral and/or a cellular immune response) but also protects against infection (i.e. fewer successful colonizations), resulting in a protective immunity. In addition, the strain is easily distinguishable, phenotypically as well as genetically, from virulent field strains of B. hyodysenteriae.

The strain of the present invention is an isolated live strain of B. hyodysenteriae. In a specific embodiment, the strain is an isolated, attenuated, avirulent strain. The terms "virulent" and "virulence" are used herein to describe B. hyodysenteriae strains with the ability to cause the clinical symptoms associated with diarrheal diseases. The term "live" is used herein to describe B. hyodysenteriae that are able to grow and reproduce. Accordingly, the live B. hyodysenteriae strain of the present invention should be able to colonize the colon of an subject but not cause the clinical symptoms (e.g. as described herein) associated with B. hyodysenteriae infection. Further, the strain of the present invention is capable of limited replication in the vaccinated subject and of inducing an immune response which is (at least partly or significantly) protective against virulent strains of B. hyodysenteriae.

The term "strain", as used herein, describes variants of a bacterial species that can be distinguished by one or more characteristics, such as ribosomal RNA sequence variation, DNA polymorphisms, serological typing, or toxin production, from other strains within that species. In the present invention B. hyodysenteriae strains can be distinguished by their virulence status, i.e. strains are classified as virulent or avirulent. Examples of virulent B. hyodysenteriae strains include WA1, B204, Vic2, BW1, NSW5, QH17 and NSW15, while examples of avirulent strains include $B78^T$, SA2206, VS1, A1, B234, R301, B6933, and FM 88.90 (La et al., 2014). The whole genome sequence of the virulent B. hyodysenteriae reference strain WA1 is provided by Bellgard et al., 2009.

Brachyspira are capable of hemolysis, the degree of which has been used to characterize them, with B. hyodysenteriae showing strong beta hemolysis. In the present invention, the sequence of several hemolysis associated genes were compared between 10 different B. hyodysenteriae strains. The strain of the present invention is characterized in that it contains at least one, including two or three, of the genes comprising or consisting of the nucleic acid sequence given in SEQ ID NO: 1, SEQ ID NO: 2 or SEQ ID NO: 3. In a further embodiment, the strain of the invention is characterized by the presence of one or more, including two or three, further genes comprising or consisting of the nucleic acid sequence given in SEQ ID NO: 4, SEQ ID NO: 5 or SEQ ID NO: 6. More particular, the strain is characterized by the presence of the hemolysis associated genes represented by SEQ ID NO: 1, SEQ ID NO: 2, SEQ ID NO: 3, SEQ ID NO: 4, SEQ ID NO: 5 and SEQ ID NO: 6, and optionally further comprises one or more of the gene(s) comprising or consisting of the nucleic acid sequence given in SEQ ID NO: 7, SEQ ID NO: 8 or SEQ ID NO: 9. More particular, the strain of the invention comprises the genes containing the nucleic acid sequence depicted in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and SEQ ID NO: 9. Furthermore, the present invention also encompasses strains comprising one or more genes, including two, three, four, five, six, seven or eight, and preferably all genes, having a nucleic acid sequence substantially identical to the nucleic acid sequence given in SEQ ID NO:1, SEQ ID NO:2, SEQ ID NO:3, SEQ ID NO: 4, SEQ ID NO: 5, SEQ ID NO: 6, SEQ ID NO: 7, SEQ ID NO: 8 or SEQ ID NO: 9. As used herein, the term "substantially identical" refers to equivalent nucleic acid sequences to those depicted in either one or all of SEQ ID NO:1 to 9 but that differ by one or more nucleotide substitutions, additions or deletions, such as allelic variants, and will also include sequences that differ due to the degeneracy of the genetic code. Hence, substantially identical sequences include sequences that are at least about 90% or 95% identical, i.e. at least 91%, 92%, 93%, 94%, 95%, 96%, 97%, 98%, or 99% identical, over the total length of the nucleic acid sequences represented by any one (or the combination) of the specific SEQ ID NOs as provided herein. Remarkably, the avirulent strain of the invention comprises the plasmid based virulence associated genes thereby differing from presently known avirulant strains that typically lack said plasmid based virulence associated genes. The nucleic acid sequence of the plasmid encoded virulence associated genes are substantially identical or identical to BHWA1_02678, BHWA1_02679, BHWA1_02680 and $BHWA1_{13}$ 02681 as characterized in reference strain WA1.

In a further embodiment, the isolated B. hyodysenteriae strain comprises a DNA genome (or genes) encoding one or more polypeptides (proteins) comprising or consisting of the amino acid sequence selected from the group consisting of SEQ ID NO: 10, SEQ ID NO:11 and SEQ ID NO:12. More in particular, the isolated *B. hyodysenteriae* strain comprises a DNA genome encoding one or more, including two or three, of the polypeptides selected from the group of amino acid sequences consisting of SEQ ID NO: 10, SEQ ID NO:11 and SEQ ID NO:12. More particular, the strain comprises a DNA genome (or genes) encoding one or more (including all) hemolysin associated polypeptides comprising or consisting of the amino acid sequence represented by SEQ ID NO: 10, SEQ ID NO: 11, SEQ ID NO: 12, SEQ ID NO: 13, SEQ ID NO: 14 or SEQ ID NO: 15, and optionally further comprises one or more of the or genes encoding the polypeptides comprising or consisting of the amino acid sequence represented by SEQ ID NO: 16, SEQ ID NO: 17 or SEQ ID NO: 18. Furthermore, the present invention also encompasses strains characterized by one or more of the polypeptides, including two, three, four, five, six, seven or eight, and preferably all polypeptides, having an amino acid sequence substantially identical to the amino acid sequence given in SEQ ID NO:10, SEQ ID NO: 11, SEQ ID NO: 12, SEQ ID NO: 13, SEQ ID NO: 14, SEQ ID NO: 15, SEQ ID NO: 16 and/or SEQ ID NO: 17. Substantially identical refers to a sequence having at least about 90% or 95%, i.e. at least 91%, 92%, 93%, 94%, 95%, 96%, 97%, 98% or 99%, sequence identity with the amino acid sequence represented by any one or all of SEQ ID NOs: 10 to 17. The term "sequence identity" alternatively referred to as "identity" as used herein refers to the percentage of sequence identity between two polypeptide sequences and/or two polynucleotide sequences, for which methods of determining are known in the art (e.g. NCBI/BLAST).

In a further embodiment, the present invention relates to the bacterial strain deposited on 23 Oct. 2015 with the International Depository Authority: the Belgian Co-ordinated Collections of Micro-Organisms (BCCM/LMG Bacteria Collection), Laboratorium voor Microbiologie, Universiteit Gent (UGent), K. L. Ledeganckstraat 35, B-9000 Gent, Belgium, and having deposit number LMG P-29184. Specifically, said strain is genetically and/or functionally different from known strains B78$^T$, SA2206, VS1, A1, B234, R301, B6933, FM88.90, and other strains described in Black et al., 2015. For example, the nucleotide sequence of the gene BHWA1_RS02195 in strain BVF1 differs 41 nucleotides from that in strain B78$^T$ (JXNF01000009.1); the nucleotide sequence of the gene BHWA1_RS02195 in strain BVF1 differs 41 nucleotides from that in strain B6933 (JXNE01000029.1); the nucleotide sequence of the gene BHWA1_RS02195 in strain BVF1 differs 37 nucleotides from that in strain FM88.90 (JXNJ01000024.1).

The strain of the present invention may also be used in the preparation of a pharmaceutical composition, in particular a vaccine composition. In some embodiments said composition comprises at least one of the strains of *B. hyodysenteriae* as described herein and a pharmaceutically acceptable carrier. It is accordingly an object of the present invention to provide a (pharmaceutical) composition or a vaccine against *Brachyspira*, in particular *Brachyspira hyodysenteriae* comprising:

a strain according to the invention; and
a pharmaceutically acceptable carrier.

The phrase "pharmaceutically acceptable" refers to molecular entities and compositions that are physiologically tolerable and do not typically produce an allergic or similarly untoward reaction, such as gastric upset and the like, when administered to the subject. More particular, the *Brachyspira* strains of the present invention are used as vaccines, such as attenuated live vaccines. It is well established that live attenuated micro-organisms are highly effective vaccines; immune responses elicited by such vaccines are often of greater magnitude and of longer duration than those produced by non-replicating immunogens. One explanation for this may be that live attenuated strains establish limited infections in the host and mimic the early stages of natural infection. In addition, unlike killed preparations, live vaccines are often more potent in inducing mucosal immune responses and cell-mediated responses, which may be connected with their ability to replicate in epithelial cells and antigen-presenting cells, such as macrophages. However, some concerns remain over the safety of using live-attenuated vaccines. Surprisingly, it has been demonstrated in the present invention that the vaccine strains and methods as described herein do not cause clinical symptoms of diarrhea and does not influence growth of the vaccinated subject, thereby significantly improving the safety of such live vaccines. With the term "vaccine" is meant a biological preparation that elicits an immune response in a subject to which the vaccine has been administered. Preferably, the immune response confers some beneficial, or protective effect to the subject against a subsequent challenge with the infectious agent. More preferably, the immune response prevents the onset of, or ameliorates at least one symptom of a disease associated with the infectious agent, in particular *B. hyodysenteriae*, or reduces the severity of at least one symptom of a disease associated with the infectious agent (such as *B. hyodysenteriae*) upon subsequent challenge.

The strains of the present invention can be administered in dosages and by techniques well known to those skilled in the medical or veterinary arts, taking into consideration such factors as the age, sex, weight, species and condition of the recipient subject, and the route of administration. The route of administration can be via mucosal administration (e.g. oral, nasal, anal, vaginal), via a parenteral route (intradermal, intramuscular, subcutaneous, intravenous, or intraperitoneal), or percutaneous. Strains can be administered alone, or can be co-administered or sequentially administered with other treatments or therapies. Forms of administration may include suspensions, syrups or elixirs, and preparations for parenteral, subcutaneous, intradermal, intramuscular or intravenous administration (e.g. injectable administration) such as sterile suspensions or emulsions.

Strains may be administered as a spray or mixed in food and/or water or delivered in admixture with a suitable carrier. The term "carrier" refers to a diluent, adjuvant, excipient, or vehicle with which the strain is administered. Such pharmaceutical carriers can be sterile liquids, such as water and oils, including those of petroleum, animal, vegetable or synthetic origin, such as peanut oil, soybean oil, mineral oil, sesame oil and the like. Water or (physiological) saline solutions and aqueous dextrose and glycerol solutions are preferably employed as carriers, particularly for injectable solutions. The composition may contain auxiliary substances such as wetting or emulsifying agents, pH buffering agents (such as e.g. citrate buffer (pH 7.0) containing sucrose, bicarbonate buffer (pH 7.0) alone, or bicarbonate buffer (pH 7.0) containing ascorbic acid, lactose, and optionally aspartame), adjuvants, gelling or viscosity enhancing additives, preservatives, flavoring agents, colors, and the like, depending upon the route of administration and the preparation desired. Standard pharmaceutical texts, such as "Remington's Pharmaceutical Sciences" (1990), 18th Edition (Mack Publishing Co.), may be consulted to prepare suitable preparations without undue experimentation. The particular pharmaceutically acceptable excipients or diluents employed are not critical to the present invention, and are conventional in the art. The compositions may be prepared in liquid form, or may be in dried powder, such as lyophilised form.

In a further embodiment the invention provides a pharmaceutical composition or vaccine comprising a therapeutically effective amount of the strain or composition described herein. The phrase "therapeutically effective amount" is used herein to mean an amount sufficient to (significantly) reduce or prevent one or more clinical symptoms associated with infection, such as but not limited to mucohaemorrhagic diarrhea, inflammation of the large intestine (cecum and/or colon), and weight loss; and/or to reduce the number of infected subjects and/or to reduce the degree of infection per subject.

The composition may be formulated for oral, parenteral, intramuscular, intravenous, subcutaneous, intraocular, or transdermal administration. In particular, the strain or composition as described herein will be delivered to the subject by oral administration, and e.g. mixed in food and/or water. The routes of administration described are intended only as a guide since a skilled practitioner will be able to determine readily the optimum route of administration and any dosage for any particular subject and condition.

As is known to the skilled person, the dose or amount varies according to the route of administration. Those skilled in the art may find that the effective dose for a vaccine administered parenterally may be smaller than a similar vaccine which is administered via drinking water, and the like. The number of microorganisms that are required to be present in the formulations can be determined and optimised by the skilled person. However, in general, a subject may be administered approximately $10^6$-$10^{12}$ colony-forming units (CFUs), preferably $10^7$, $10^8$, $10^9$, $10^{10}$ or $10^{11}$ CFUs in a single dosage unit.

The compositions as disclosed in the embodiments of the invention may be part of a kit. More specific, the kit comprises a lyophilized or freeze dried vaccine strain formulation. One or more strains of B. hyodysenteriae as described herein can be cultured in appropriate medium and allowed to grow to the desired level. The pooled bacterial broth can be mixed with a stabilizer composition (e.g. trehalose, sorbitol, sucrose, foetal bovine serum, anti-oxidantia) in appropriate ratio and then can be subjected to a drying process. The drying can be effected by freeze dryer or spray dryer. Typically the kit would also include instructions for use.

The composition or vaccine of the present invention is highly suitable for protecting animals against Brachyspira infection, in particular infection with B. hyodysenteriae. The Brachyspira hyodysenteriae strains of the invention, and composition or vaccine comprising the same, are highly suitable for immunizing veterinary species, in particular pigs. In said respect, the strain or composition can e.g. be administered to early weaned pigs. The administration may take place in a single dose or in a dose repeated once or several times after a certain period.

It is thus an object of the present invention to provide the use of strains of B. hyodysenteriae of the present invention for preparing a medicament which is employed for the prophylactic treatment of Brachyspira hyodysenteriae infection in a subject, more particular in animals, even more particular in pigs. The present invention thus also encompasses the strains of B. hyodysenteriae as described herein for treating, reducing (the risk of) and/or preventing diarrhea, in particular mucohemorrhagic diarrhea, even more particular diarrhea associated with swine dysentery. The invention thus also provides a method of treating swine dysentery and a method of preventing or reducing spread of B. hyodysenteriae in a pig population.

The strain as described herein is easy distinguishable from virulent field strains by quantitative real-time PCR (qPCR). The present invention also relates to a method of diagnosing or screening for avirulent B. hyodysenteriae colonization in a subject. In some embodiments the method comprises obtaining a sample from a subject suspected of having a B. hyodysenteriae infection. A "sample" refers to tissue, biological fluids or other materials suspected of containing B. hyodysenteriae, or its polynucleotides or its polypeptides. Examples of such tissues, fluids or materials include, but not limited to, plasma, serum, fecal material, urine, biopsy material including stomach and intestine samples. The sample might also include in vitro cell culture constituents.

Whether a subject is colonized with an avirulent strain of B. hyodysenteriae may be determined by assessing the presence or absence of the polynucleotides/genes or proteins as described herein, or by determining the presence of specific mutations as described herein. The presence of a gene may be determined by the analysis of any factors associated with or indicative of transcription and translation of a gene including, but not limited to RNA expression levels and protein expression levels, as well as the presence of the DNA sequence within the genome. Techniques for identifying the presence of a gene or its product in a sample are known by one skilled in the art. Routine techniques such as Northern and Western blotting, PCR, microarrays and ELISAs are known in the art.

In a specific embodiment, the invention provides a method of diagnosing avirulent B. hyodysenteriae colonization in a subject, comprising the steps of: (a) obtaining a sample from said subject; and (b) determining the presence or absence of one or more polynucleotide sequences comprising the nucleic acid sequence(s) depicted in any one or all of SEQ ID NOs:1 to 6, or a sequence substantially identical thereto, and/or the expression of one or more corresponding mRNA or encoded protein product(s), such as depicted in SEQ ID NOs: 10 to 15, or a sequence substantially identical thereto; wherein the presence of said nucleic acids or corresponding mRNA or protein products indicates the presence of avirulent B. hyodysenteriae colonization in the subject.

In a further embodiment, the invention provides a method of identifying a candidate vaccine strain of B. hyodysenteriae comprising the steps: (a) obtaining a sample of B. hyodysenteriae; and (b) determining the presence or absence of one or more or all of the nucleic acid molecules as depicted in SEQ ID NOs:1-6, or a sequence substantially identical thereto, and/or the expression of corresponding mRNA or protein products such as e.g. represented by SEQ ID NOs: 10-15, or a sequence substantially identical thereto, wherein the presence of said one or more nucleic acids or expression of corresponding mRNA or protein, is indicative of a vaccine strain of B. hyodysenteriae.

The following examples are set forth below to illustrate the methods, compositions, and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

EXAMPLES

Materials and Methods

1. Isolation of BVF1 and Identification

Fresh fecal samples were collected from pigs on a farm in Flanders and cultured within 12 hours after sampling on selective plates consisting of Trypticase Soy Agar (TSA) supplemented with 5% sheep blood, 1% yeast extract, 25 µg/ml vancomycin, 400 µg/ml spectinomycin and 25 µg/ml colistin. Isolates were purified by three to five subcultures on Trypticase Soy Agar (TSA) plates supplemented with 5% sheep blood and 1% yeast extract and eventually stored at −70° C. until further use.

Phenotypic characterization was performed on pure 4-day old cultures and was based on beta hemolysis, indole production, hippurate hydrolysis and the presence or absence of α-galactosidase and β-glucosidase. Indole production was determined using a spot-indole test (Remel BactiDrop, Dartford, UK). For the other biochemical characteristics, commercial discs were used according to the manufacturer's instructions (Rosco Diatabs, Taastrup, Denmark). Type strains of B. hyodysenteriae (ATCC 27164), B. pilosicoli (ATCC 51139) and B. innocens (ATCC 29796) were included to provide positive controls for all the phenotypic characteristics that were examined.

Several species-specific PCRs were performed, based on the following genes: tlyA, 23S rRNA and nox. The NADH oxidase (nox) gene and 16S rRNA gene were partially sequenced by using the following primers for 16S: kag-007 forward 5'GTTTGATYCTGGCTCAGARCKAACG3' (SEQ ID NO: 18), kag-009 reverse 5'CTTCCGGTACG-GMTGCCTTGTTACG3' (SEQ ID NO: 19) and following primers for nox: Br-NOX1-F 5' TAGCYTGCGG-TATYGCWCTTT3' (SEQ ID NO: 20), Br-NOX3-R 5'GCMTGWATAGCTTCRGCATGRT3' (SEQ ID NO: 21) (Johansson K. et al., 2004; Weissenböck H. et al., 2005). The sequences retrieved from strain BVF1 were compared by BLAST analysis to known sequences of B. hyodysenteriae type- and reference strains. Strain BVF1 has been deposited on 23 Oct. 2015 with the International Depository Authority: the Belgian Co-ordinated Collections of Micro-Organisms (BCCM/LMG Bacteria Collection), Laboratorium voor Microbiologie, Universiteit Gent (UGent), K. L. Ledeganckstraat 35, B-9000 Gent, Belgium and has deposit number LMG P-29184.

2. In Vitro Hemolysis Assay

The hemolytic capacity of B. hyodysenteriae strain BVF1 and 9 other B. hyodysenteriae field strains, isolated from Belgian swine herds, was compared in an in vitro hemolysis assay. Fresh blood was collected from 8 week old pigs and a volume of blood was immediately mixed with an equal volume of Alsever's solution (50/50 v/v). This blood-Alsever's mixture was washed three times with Dextrose-Glucose-Veronal (DGV) buffered solution and the hematocrit of the suspension was determined using a microhematocrit centrifuge and reader. DGV buffered solution was added until a 10%-suspension of red blood cells was obtained.

Fresh cultures of the different B. hyodysenteriae isolates were prepared and incubated for 24 hours under anaerobic conditions at 37° C. on a rocking platform. For each strain three cultures were made. After incubation, cultures were microscopically examined for purity and the Optical Density at 620 nm (OD620) was measured. Cultures were only retained if their OD620 measured between 0.30 and 0.35. Supernatant was collected by centrifugation at 500 g for 20 minutes and was filter-sterilized. The strongly hemolytic strain B204 (ATCC 31212) served as a reference strain in the in vitro hemolysis assay.

The hemolysis assay was performed in 96-well U-bottom microtiter plates. After pipetting 100 µl of the 10% red blood cell suspension in each well, 100 µl of the filtered B. hyodysenteriae culture supernatant was added. Triton-X 2% served as a positive control (complete hemolysis) and DGV served as a negative control (no hemolysis). Plates were incubated for two hours at 37° C. in a 5% CO2 atmosphere. After incubation the absorption of the supernatant fluid was determined using an ELISA-reader (450 nm). All assays were performed in triplicate and repeated three times.

3. Sequencing of Hemolysis Associated Genes

Complete sequences of the hlyA, tlyA, tlyB, tlyC, BHWA1_RS02885 (hemolysin activation protein), BHWA1_RS02195 (hemolysin III) and BHWA1_RS09085 (hemolysin III channel protein) genes were determined for all B. hyodysenteriae strains that were used in the in vitro hemolysis assay. For hlyA, the ACP1-Fo and ACP1-Re primers were used as described by Barth et al., 2012 For tlyA, the primers were designed based on the sequences of tly (GenBank: X61684.1 GI:296624) (tlyA was originally named tly as it was presumed to be the only hemolysin of Brachyspira) as deposited by Muir et al., 1992, and the whole genome sequence of B. hyodysenteriae WA1 (GenBank: NC_012225.1 GI:225618950). The tlyB and tlyC primers were based on the sequences (GenBank: X73140.1 GI:511144) (tlyB), (GenBank: X73141.1 GI:511146) (tlyC) and their alignment with the whole genome sequence of WA1 respectively. Primers for BHWA1_RS02885, BHWA1_RS02195 and BHWA1_RS09085 were designed based on their sequence as deposited in GenBank (GenBank: NC_012225.1 GI:225618950). Primers, position as given in the whole genome sequence of WA1 (GenBank: NC$_{13}$ 012225.1 GI:225618950), product length and annealing temperature are shown in Table 1.

TABLE 1

Primers, position, product size and annealing conditions for detection of hemolysis related genes tlyA, tlyB, tlyC, BHWA1_RS02885, BHWA1_RS02195 and BHWA1_RS09085.

| Target gene and primer names | Nucleotide sequence (5'→3') | Position (NC_012225.1) | Product size (bp) | Temperature annealing (° C.) |
|---|---|---|---|---|
| tlyA: hemolysin A | | | | |
| tlyAS1Fo | GGTATTGGAGATGAATATAC (SEQ ID NO: 22) | 267034-267054 | 956 | 58 |
| tlyAS1Re | TGATGTAGAAGGCTTCTATA (SEQ ID NO: 23) | 267969-267989 | | |
| tlyB: hemolysin B | | | | |
| tlyBS3Fo | GGAGTGGAGAGAAAGTATTA (SEQ ID NO: 24) | 1414613-1414633 | 974 | 57 |
| tlyBS3Re | TGCTGTAAGCAGACTTATAG (SEQ ID NO: 25) | 1415566-1415586 | | |
| tlyBS4Fo | AGCTGTCCTTCTTCAAGTAC (SEQ ID NO: 26) | 1415413-1415433 | 390 | 63 |
| tlyBS4Re | AGTCGTAGGACAGAAAGAAG (SEQ ID NO: 27) | 1415782-1415802 | | |
| tlyBS2Fo | CCCTCTTCATAACCAACATA (SEQ ID NO: 28) | 1415533-1415553 | 1062 | 65 |
| tlyBS2Re | AGGGACTTGCTGAAAAGATA (SEQ ID NO: 29) | 1416653-1416673 | | |
| tlyBS1Fo | TTGTACCAGCAACAACTGAA (SEQ ID NO: 30) | 1416575-1416595 | 1082 | 54 |
| tlyBS1Re | AGCTCTATCTACAGCAATAC (SEQ ID NO: 31) | 1417635-1417655 | | |
| tlyC: hemolysin C | | | | |
| tlyCFo | TTACGAATGCCTGCTATTTG (SEQ ID NO: 32) | 1644915-1644935 | 1131 | 50 |
| tlyCRe | CTATTTTTAGGCGAGGCTTT (SEQ ID NO: 33) | 1646025-1646045 | | |
| BHWAI_RS02885: hemolysin activation protein | | | | |
| HlysCBSFo | GGAAAAAGGGATCCTGGAAC (SEQ ID NO: 34) | 704725-704745 | 1570 | 54 |
| HlysCBSRe | TCCTGCTTGTTATCAGCACA (SEQ ID NO: 35) | 706278-706298 | | |
| BHWAI_RS02195: hemolysin III | | | | |
| Hlys3-1Fo | CTATTGGAGAGCGTACATCT (SEQ ID NO: 36) | 503577-503597 | 1014 | 58 |
| Hlys3-1Re | TACCCTGTACCTACAGAACA (SEQ ID NO: 37) | 504571-504591 | | |
| BHWAI_RS09085: hemolysin III channel protein | | | | |
| Hlys3-2Fo | CTCCTCCCGTTCAATATGTA (SEQ ID NO: 38) | 2156200-2156220 | 974 | 58 |
| Hlys3-2Re | AATCCGCCATGTAAAACTGC (SEQ ID NO: 39) | 2157154-2157174 | | |

PCR was performed under standard conditions in a 25 µl reaction volume with Taq polymerase (Bioline, Taunton, USA). The PCR program started with 95° C. for 15 minutes, followed by 35 cycles of 95° C. for 30 seconds, 1 minute at the primer specific annealing temperature and 72° C. for 1 minute. The final extension step was 72° C. for 2 minutes after which samples were cooled to 4° C. Optimal annealing temperatures are given for each primer pair in table 1. For all strains, the sequences were compared to each other and to previously deposited sequences with BLAST analysis.

4. Comparison of Pathogenicity for Pigs of B. hyodysenteriae Strain BVF1 and Several Strongly Hemolytic B. hyodysenteriae Strains Three strongly hemolytic B. hyodysenteriae strains and weakly hemolytic B. hyodysenteriae strain BVF1 were used to inoculate pigs in five independent experimental infection trials. Experimental model, inoculation route, strain and number of pigs are given in table 2.

TABLE 2 experimental set-up in vivo trials

| Experiment number | B. hyodysenteriae strain | Model | Inoculation route | Soy feed regime | Number of pigs |
|---|---|---|---|---|---|
| 1 | 8dII | direct inoculation | oral | yes | 6 |
| 2 | B204 | direct inoculation | intragastric | no | 9 |
| 3 | 49 | seeder model | / | no | 20 |
| 4 | BVF1 | direct inoculation | oral | yes | 8 |
| 5 | BVF1 | direct inoculation | intragastric | no | 12 |

All pigs were purchased from a commercial farm, which had no history of swine dysentery. Pigs were acclimatized for at least one week and had ad libitum access to water and a commercial starter feed. In some trials a soy feed regime was applied at the time of inoculation to enhance the development of infection. During this soy feed regime each second half of the day, the commercial starter food was replaced by a pure soybean meal. Inoculations were all preceded by a 12 h fast. Inoculation cultures were grown for 48 hours under anaerobic conditions on a rocking platform at 37° C.

In all experiments fecal samples were collected three times a week after inoculation. DNA was extracted from the fecal samples using QIAamp Fast DNA Stool kit (Qiagen, Hilden, Germany) and the extracted DNA was used to determine the presence and the quantity of B. hyodysenteriae DNA with qPCR. At the time of sampling feces were scored. Fecal scores were determined as 0: normal, 1: softer but formed, 2: unformed semi-wet, 3: runny, 3.5: runny with mucus or blood, 4: runny with mucus and blood.

The correlation of fecal excretion and fecal scores was determined for the in the in vivo experiments with the strongly hemolytic B. hyodysenteriae strains and for the in vivo experiments with strain BVF1.

5. PCRs for the Presence of Plasmid Genes

The presence or absence of plasmid encoded genes was determined for all isolates that were used in the in vivo trials. Strain B204 (ATCC 31212) was used as a positive control. PCRs were performed for three plasmid genes positioned around the plasmid's origin of replication: BHWA1_02686, BHWA1_02687, and BHWA1_13 02688 [La et al., 2011]. Additionally, PCRs were performed for the plasmid encoded virulence associated genes BHWA1_02678, BHWA1_02679, BHWA1_02680 and BHWA1_02681 as well. These virulence associated genes encode a radical S-adenosyl methionine protein, a glycosyltransferase, an NAD-dependent epimerase and an dTDP-4-dehydrorhamnose 3,5 epimerase (rfbC) respectively [La et al., 2011, La et al., 2014]. For each of these 7 plasmid genes, three primer pairs were used, as described previously by La et al. (2011, 2014). Besides the previously described primer pairs, combinations of the three primer pairs were also used if applicable, for example the forward primer BHWA1_02680a-F in combination with the reverse primer BHWA1_02680b-R.

| Gene | Alternative name | Position in NC_012226.1 (whole genome of pBHWA1 (plasmid of *B. hyodysenteriae* strain WA1)) |
|---|---|---|
| BHWA1_02678 | BHWA1_RS13010 | 15095 . . . 16105, complement |
| BHWA1_02679 | BHWA1_RS13015 | 16246 . . . 17511 |
| BHWA1_02680 | BHWA1_RS13020 | 17508 . . . 18368, complement |
| BHWA1_02681 | BHWA1_RS13025 | 18371 . . . 18904, complement |

Protective Capacity of *B. hyodysenteriae* Strain BVF1 in a Swine Vaccination Model In this vaccination experiment 21 pigs of five weeks old were purchased from a commercial farm, free of swine dysentery. Animals were randomly assigned to two groups: animals 1-12 vaccinated group, animals A-I non-vaccinated group. Animals were weighed weakly and were provided with a commercial starter feed.

At day −2, −1 and 0 the vaccination group was inoculated intragastrically with 20 ml inoculum of strain BVF1 containing ≈$10^9$ bacteria/ml. On the same days the non-vaccination group was sham inoculated intragastrically with 20 ml of sterile culture medium. At day 19, 20 and 21 all animals were inoculated intragastrically with a virulent *B. hyodysenteriae* strain B204. All animals received 20 ml inoculum of strain B204 containing ≈$10^9$ bacteria/ml on three consecutive days.

All animals were monitored daily for the presence of clinical signs. Three times a week fecal samples were collected and feces were scored. DNA was extracted from all fecal samples using QIAamp Fast DNA Stool kit (Qiagen, Hilden, Germany) and the extracted DNA was used to determine the quantity of *B. hyodysenteriae* DNA with qPCR. Animals were euthanized 24 hrs after the first signs of swine dysentery. Animals that showed no signs of dysentery were euthanized at day 40 (19 days post challenge with *B. hyodysenteriae* B204).

In order to specifically determine the quantity of *B. hyodysenteriae* DNA of the vaccine strain BVF1 and of the challenge strain B204 in the feces of vaccinated and challenged animals, primers were designed to specifically anneal with DNA of either strain BVF1 or strain B204. Specific primers for each strain were based on the BHWA1_RS02885 gene (hemolysin activation protein). Primers detecting strain BVF1 are HlyVacFo 5'TGGTGAAATACTGCCAAA3' (SEQ ID NO: 40) and HlyVacRe 5'TGTTGTTATATCGTC-CATAC3' (SEQ ID NO: 41), primers detecting strain B204 (and all strongly hemolytic strains used in the hemolysis in vitro study) are HlyInfFo 5'GTTAATGCTGAAAAAAT-GATG3' (SEQ ID NO: 42) and HlyInfRe 5'AAGCTCTTG-TATGGAATATAC3' (SEQ ID NO: 43). Both primer pairs were used in a separate qPCR reaction since both primer pairs generated a melt temperature of 74.5° C. and could not be distinguished based on their melt temperature.

For generation of the standards, part of the BHWA1_RS02885 gene was amplified (636 bp) using primers HlysSTFo 5'CAAGTTCTATGATACCTAC3' (SEQ ID NO: 44) and HlysSTRe 5'GCCGCCTTTAACATAY-TCTTT3' (SEQ ID NO: 45). For each *B. hyodysenteriae* strain separate standards were prepared. The standard consisted of 10-fold-dilutions starting at $10^8$ PCR amplicons for each 10 µL of reaction mixture. Two µL of extracted DNA template was suspended in a 10 µL reaction mixture consisting of 0.25 µL of both primers 3.5 µL HPLC water and 5 µL SensiMix™ SYBR No-ROX (Bioline Reagents Ltd, UK). The PCR program consisted of denaturation for 10 min at 95° C., followed by amplification cycles at 95° C. for 30 s, annealing at 60° C. for 30 s and extension at 73° C. for 30 s.

Both standards and samples were run in duplicate on a CFX96™ RT-PCR System with a C1000 Thermal Cycler (Bio-Rad, Hercules Calif., USA). The Bio-Rad CFX Manager (version 1.6) software was used for calculation of threshold cycles (Ct)-values and melting curve analysis of amplified DNA. The average values of the duplicates were used for quantification of *B. hyodysenteriae* strain BVF1 or B204 DNA in the fecal samples.

7. Validation of the Protective Capacity of *Brachyspira Hyodysenteriae* Strain BVF1 in a Seeder Model for Pigs Infection and disease dynamics of swine dysentery between vaccinated and non-vaccinated pigs were compared in a seeder model. In this seeder model, half of the pigs are inoculated with the challenge strain of *B. hyodysenteriae* ("seeders"). These seeders are accompanied by pigs ("receivers") that are not inoculated and can thus contract infection in a way, similar to that on an infected farm. Sixty pigs of six weeks old were purchased from a commercial farm, free from swine dysentery. The animals were randomly divided into 6 groups, resulting in three replicates per treatment. Each group contained 5 seeder animals and 5 receiver animals.

| Group 1V vaccinated 5 seeders/5 receivers | Group 2V vaccinated 5 seeders/5 receivers | Group 3V vaccinated 5 seeders/5 receivers |
|---|---|---|
| Group 1NV non-vaccinated 5 seeders/5 receivers | Group 2NV non-vaccinated 5 seeders/5 receivers | Group 3NV non-vaccinated 5 seeders/5 receivers |

At days −2, −1, and 0, all pigs in vaccinated groups 1V, 2V, 3V were inoculated ("vaccinated") orally with 20 ml inoculum of strain BVF1 containing ≈$10^9$ bacteria/ml. On the same days all pigs in non vaccinated groups NV1, NV2, and NV3 were sham vaccinated orally with 20 ml of sterile culture medium. Three times per week fecal samples were collected and fecal consistency was scored. DNA was extracted from all fecal samples using QIAamp Fast DNA Stool kit (Qiagen, Hilden, Germany) and the extracted DNA was used to determine the quantity of *B. hyodysenteriae* vaccine strain BVF1 DNA with qPCR.

At days 19, 20 and 21 all seeder animals in each group (V1, V2, V3, NV1, NV2, NV3) were inoculated orally with a virulent *B. hyodysenteriae* strain B204 ("challenge"). All seeder animals received 20 ml inoculum of strain B204 containing ≈$10^9$ bacteria/ml on three consecutive days. These animals acted as "seeder animals" that may spread *B. hyodysenteriae* to their pen mates. The pen mates that are not inoculated with the virulent challenge strain are designated as the "receiver animals".

All animals were monitored daily and two times per week fecal samples were collected and fecal consistency was scored. DNA was extracted from all fecal samples using QIAamp Fast DNA Stool kit (Qiagen, Hilden, Germany) and the extracted DNA was used to determine the quantity of *B. hyodysenteriae* strain B204 with qPCR.

Animals were euthanized at day 52, 53, or 54 which is 31, 32 or 33 days after challenge with the virulent *B. hyodysenteriae* strain B204. Animals were euthanized prior to the end of the experiment when severe anorexia, severe apathy, or fever >40° C. was present.

Results

1. Species Identification of Strain BVF1

Results for the phenotypic characterization and species-specific PCR's are given in tables 3 and 4. Phenotypically strain BVF1 would be identified as *B. intermedia* due to the weak hemolysis shown on agar plate. However, species-specific PCR's identify strain BVF1 as *B. hyodysenteriae*. The sequence comparison of the 16S rRNA and nox gene of strain BVF1 with known sequences of *B. hyodysenteriae* type- and reference strains, definitively identifies strain BVF1 as *B. hyodysenteriae:* 16S rRNA and nox show 100% similarity with previously deposited strains of *B. hyodysenteriae*.

TABLE 3 phenotypic characterization of strain BVF1, compared to typestrains of
B. hyodysenteriae and B. intermedia.

| | hemolysis | Indole production | Hippurate hydrolysis | α-galactosidase | β-glucosidase |
|---|---|---|---|---|---|
| Strain BVF1 | weak | + | − | − | + |
| B204 typestrain B. hyodysenteriae | strong | + | − | − | + |
| PWS/A typestrain B. intermedia | weak | + | − | − | + |

TABLE 4 results of species-specific PCR's for strain BVF1, compared to
typestrains of B. hyodysenteriae and B. intermedia. Genes targeted
by PCR are given for each species.

| | B. hyodysenteriae | | | B. intermedia | |
|---|---|---|---|---|---|
| | nox | tlyA | 23S | nox | 23S |
| Strain BVF1 | + | + | + | − | − |
| B204 typestrain B. hyodysenteriae | + | + | + | − | − |
| PWS/A typestrain B. intermedia | − | − | − | + | + |

2. Strain BVF1 has Significantly Lower In Vitro Hemolytic Capacity

FIG. 1 displays the in vitro hemolysis of the described B. hyodysenteriae strains. The strength of hemolysis showed gradual variation, nevertheless most strains showed a strength of hemolysis in the same range as the B204 reference strain. For strain BVF1 the hemolysis was significantly lower than for the B204 reference strain (P<0.01).

We here provide evidence that the degree of hemolysis also varies between B. hyodysenteriae strains. After experimental inoculation, animals shedding high numbers ($10^8$ copies/g feces) of the weakly hemolytic strain BVF1 did not show any clinical signs or lesions after experimental inoculation. Differences in virulence between B. hyodysenteriae strains, not associated with hemolysis, have been demonstrated as well (Achacha et al., 1996; La et al., 2014). The absence of a set of plasmid encoded genes for example can be indicative for reduced pathogenic potential. Nevertheless, for swine dysentery diagnosis and control, the occurrence of low hemolytic and low virulent strains would have far-reaching implications.

Presence or absence of B. hyodysenteriae are currently used as sole criterion for swine dysentery diagnosis and entry control. If a herd tests positive for B. hyodysenteriae, this may influence the trading possibilities of the farm in question, even in the absence of overt clinical signs, because of the possible risk of swine dysentery carrier animals. When diagnosis is primarily based on microbial culture procedures, weakly hemolytic B. hyodysenteriae strains could be mistaken for B. intermedia. When diagnosis is primarily based on the current PCR tests, the degree of hemolysis of the specific strain cannot be estimated.

3. Strain BVF1 Shows Nucleotide and Amino Acid Changes in Several Hemolysis Associated Genes The nucleotide sequence differences and amino acid differences are summarized in tables 5 and 6.

TABLE 5

Nucleotide and amino acid differences for hemolysis related genes of
B. hyodysenteriae strains used in this study. Differences compared with the genome sequence
of B. hyodysenteriae strain WA1. Number of amino acid changes are given in brackets.

| Strain | In vitro hemolysis | tlyA 723 nt | hlyA 237 nt | tlyB 2487 nt | tlyC 807 nt | BHWA1_RS02885 1335 nt | BHWA1_RS02195 675 nt | BHWA1_RS09085 672 nt |
|---|---|---|---|---|---|---|---|---|
| 3bIII | ++ | 0 | 2 (0) | 7 (0) | 0 | 0 | 15 (5) | 2 (1) |
| 4cI | ++ | 0 | 2 (0) | 7 (0) | 0 | 0 | 15 (5) | 2 (1) |
| 8dII | ++ | 0 | 0 | 0 | 0 | 10 (0) | 15 (5) | 0 (0) |
| 10cI | ++ | 0 | 0 | 5 (0) | 0 | 0 | 14 (5) | 1 (0) |
| 21bI | ++ | 0 | 0 | 1 (0) | 0 | 0 | 15 (5) | 1 (0) |
| 25cI | ++ | 0 | 0 | 7 (0) | 0 | 0 | 14 (5) | 1 (0) |
| D1 | ++ | 0 | 0 | 5 (0) | 0 | 0 | 14 (5) | 1 (0) |
| BVF1 | +/− | 1 (1) | 0 | 2 (1) | 4 (0) | 63 (5) | 41 (8) | 12 (1) |
| M1 | ++ | 0 | 0 | 0 | 0 | 10 (0) | 15 (5) | 0 (0) |

TABLE 6

Nucleotide differences for hemolysis related genes of B. hyodysenteriae
strain BVF1 compared with the genome sequence of several avirulent
strains of B. hyodysenteriae.

| Strain | gene | Number of nucleotide differences | FASTA code gene/strain |
|---|---|---|---|
| B78 | 16S rRNA | 2 | JXNF01000063 |
| | tlyA | 1 | JXNF01000009 |
| | tlyB | 3 | JXNF01000010 |
| | tlyC | 3 | JXNF01000041 |
| | BHWA1_RS02195 | 41 | JXNF01000009 |
| | BHWA1_RS09085 | 14 | JXNF01000023 |
| | BHWA1_RS02885 | 63 | JXNF01000075 |
| B6933 | 16s rRNA | 1 | JXNE01000011 |
| | tlyA | 1 | JXNE01000076 |

TABLE 6-continued

Nucleotide differences for hemolysis related genes of *B. hyodysenteriae* strain BVF1 compared with the genome sequence of several avirulent strains of *B. hyodysenteriae*.

| Strain | gene | Number of nucleotide differences | FASTA code gene/strain |
|---|---|---|---|
| | tlyB | 9 | JXNE01000055 |
| | tlyC | 5 | JXNE01000006 |
| | BHWA1_RS02195 | 41 | JXNE01000029 |
| | BHWA1_RS09085 | 14 | JXNE01000061 |
| | BHWA1_RS02885 | 66 | JXNE01000079 |
| FM88.90 | 16s rRNA | 1 | JXNJ01000038 |
| | tlyA | 1 | JXNJ01000068 |
| | tlyB | 3 | JXNJ01000012 |
| | tlyC | 6 | JXNJ01000012 |
| | BHWA1_RS02195 | 37 | JXNJ01000024 |
| | BHWA1_RS09085 | 12 | JXNJ01000018 |
| | BHWA1_RS02885 | 57 | JXNJ01000004 |

The sequences for hlyA were similar for all strains except strain 3bIII and 4cI, which differed with regard to 2 nucleotides. However, these nucleotide differences do not translate into a different amino acid sequence. Strain BVF1 was the only strain with a nucleic acid substitution in the tlyA gene. The substitution was located at position 501 (G→T) as given in Tly (GenBank: X61684.1 GI:296624) by Muir et al., 1992, or position 267228 as in the genome sequence of WA1 (GenBank: NC_012225.1 GI:225618950) (Bellgard et al., 1992). This nucleic acid substitution translated into a different amino acid at position 10 in the amino acid sequence (Glycine→Cysteine).

The sequence of the tlyB gene showed differences between the isolates and the number of nucleotide changes varied from 1 to 7 as given in table 5. For all strains except strain BVF1 these nucleotide differences did not translate into an amino acid sequence diverging from the reference strain WA1. The sequence of the weakly hemolytic strain BVF1 differed at 2 positions of which the nucleotide change at position 1416206 (C→T) translates into an amino acid substitution at position 384 in the amino acid sequence (Alanine→Threonine).

With regard to the tlyC gene, all strains were identical except for weakly hemolytic strain BVF1 of which the tlyC sequence differed four nucleotides. Nonetheless this altered nucleotide sequence did not encode a different amino acid sequence.

The BHWA1_RS02885 (hemolysin activation protein) gene sequence showed no nucleotide differences for six of the strains. The strains 8dII and M1 share an identical sequence which diverges 10 nucleotides compared to the sequence of *B. hyodysenteriae* reference strain WA1. However, these nucleotide differences do not translate into a different amino acid sequence. Strain BVF1 showed as much as 63 nucleotide differences compared to the sequence of *B. hyodysenteriae* reference strain WA1. These nucleotide differences result in 5 amino acid substitutions at following positions: 81 (Valine→Isoleucine), 113 (Methionine→Valine), 164 (Glutamic acid→Aspartic acid), 227 (Threonine→Serine), 264 (Valine→Isoleucine).

With regard to the BHWA1_RS02195 gene (hemolysin III) it was noticed that all strains showed a difference of 14 or 15 nucleotides with the sequence of *B. hyodysenteriae* reference strain WA1 (table 5). These sequences all translated in an amino acid sequence with a difference of 5 amino acids at following positions: 51 (Proline→Serine), 56 (Valine→Isoleucine), 59 (Valine→Leucine), 82 (Leucine→Isoleucine), 93 (Valine→Isoleucine). The BHWA1_RS02195 of *B. hyodysenteriae* reference strain B204 was sequenced as well and the sequence was identical to that of strains 10cI, 25cI and D1. This results in the same amino acid sequence with 5 differences compared to *B. hyodysenteriae* reference strain WA1. Strain BVF1 showed 44 nucleotide differences compared to the sequence of *B. hyodysenteriae* reference strain WA1 (table 5), which translates into an amino acid sequence different from that of strain WA1 by 8 amino acids: 47 (Threonine→Isoleucine), 49 (Valine→Methionine), 56 (Valine→Isoleucine), 79 (Valine→Isoleucine), 82 (Leucine→Isoleucine), 111 (Valine→Isoleucine), 114 (Leucine→Proline), 133 (Methionine→Isoleucine).

The sequences for the hemolysin III channel protein gene BHWA1_RS09085 of the strains in this study were equal to that of *B. hyodysenteriae* reference strain WA1 or differed by 1 or 2 nucleotides (table 5), strain BVF1 differed by 12 nucleotides. For strains 3bIII and 4cI the nucleotide differences resulted in an amino acid substitution at position 217 (Arginine→Isoleucine), and for strain BVF1 at position 209 (Isoleucine→Valine).

The low haemolytic strain BVF1 showed marked sequence differences in most hemolysis associated genes when compared to all other strains in the study and to *B. hyodysenteriae* reference strain WA1. *B. hyodysenteriae* strain M2 is also moderately hemolytic. However, most amino acid sequences for hemolysis related genes of strain M2 are identical to the strongly hemolytic *B. hyodysenteriae* reference strain WA1. The amino acid sequence for BHWA1_RS02195 shows five differences compared to WA1. Nevertheless, the amino acid sequence is identical to that of most of the strains used in this study and the amino acid sequence of another *B. hyodysenteriae* reference strain B204. Not only a difference in amino acid sequence, which can affect the function of a protein, might influence the gradation in hemolytic capacity but there might also occur a more distant variance such as altered activity of promoter regions or altered transcription of genes under specific circumstances in vitro as well as in vivo. Although repeated subculturing can result in phenotypical changes such as loss of hemolysis (Peppler et al., 1982), already during primary isolation of strains BVF1 and M2, hemolysis was always weak and moderate respectively.

4. Fecal Excretion of *B. hyodysenteriae* BVF1 is not Correlated with Clinical Signs of Swine Dysentery In all experimental trials using strongly hemolytic *B. hyodysenteriae* strains, signs of dysentery were noted for animals that were excreting *B. hyodysenteriae* in their feces.

In experiment number 1 fecal excretion was first noted after on average 11 days post inoculation and fecal excretion lasted over 25 days (end of trial). In experiment 2 fecal excretion of challenged animals was first noted after 7 days. In this trial animals were euthanized as soon as they developed clinical dysentery, hence duration of excretion was not followed over time. In experiment 3 fecal excretion was first seen 20 days post inoculation and lasted for 21 days (end of trial).

In experiment 4 and 5 fecal excretion of strain BVF1 could first be noted after 7 or 5 days post inoculation respectively. However, no clinical signs of dysentery were noticeable. The fecal excretion of strain BVF1 was limited in time and lasted for 14 days (experiment 4) or 10 days (experiment 5).

Figure 2:
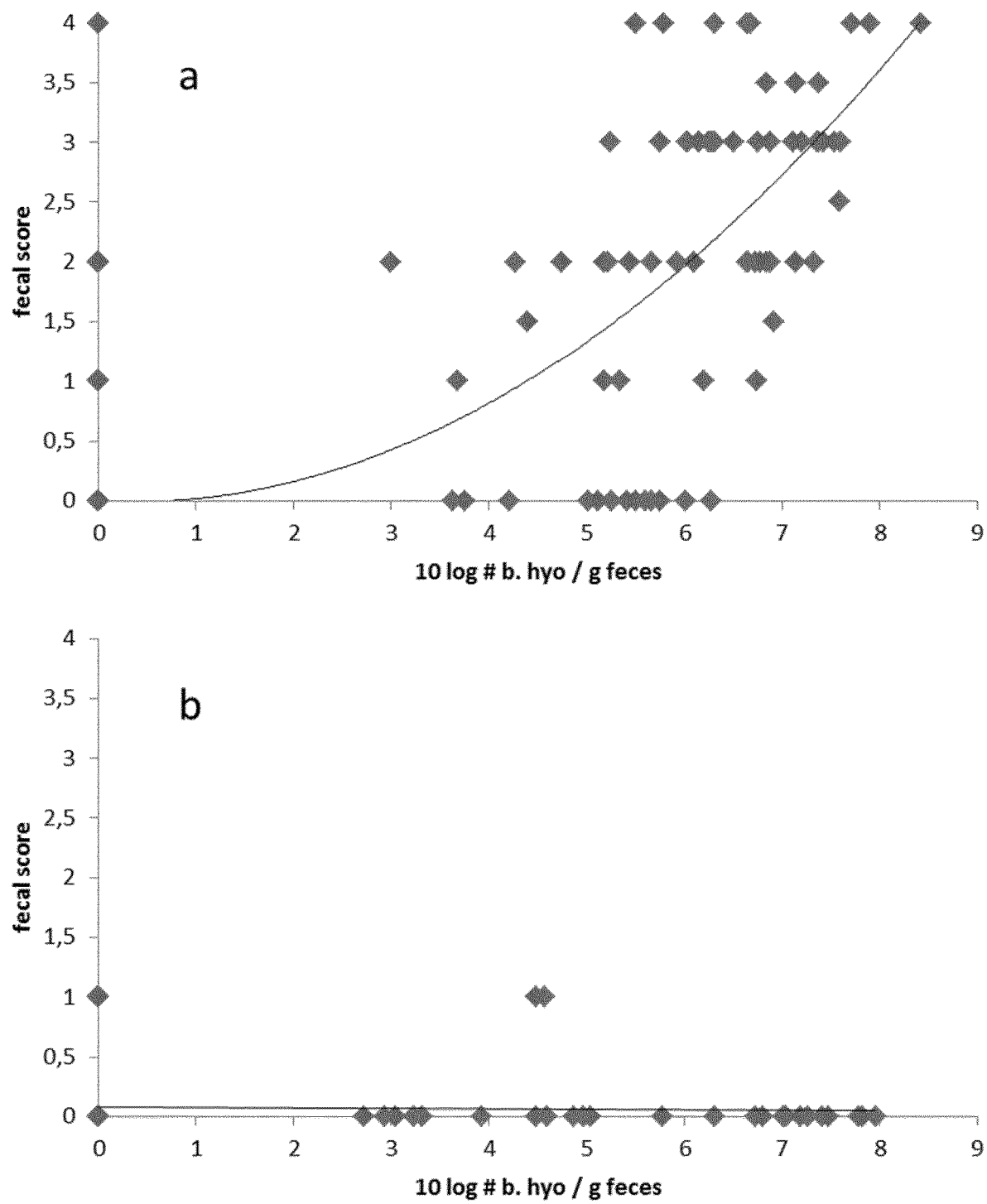
FIG. 2: Correlation between fecal excretion and fecal scores for strong hemolytic *B. hyodysenteriae* strains and for strain BVF1. Fecal scores in correlation with fecal excretion. Panel (a): strongly hemolytic *B. hyodysenteriae* strains, panel (b): strain BVF1. Fecal scores 0: normal, 1: softer but formed, 2: unformed semi-wet, 3: runny, 3,5: runny with mucus or blood, 4: runny with mucus and blood.

For the strong hemolytic *B. hyodysenteriae* strains used in experimental trial 1, 2 and 3 there is a strong correlation ($p<0.001$) between fecal excretion of the strain and the occurrence of clinical symptoms. This is shown in FIG. 2, panel A. As shown in panel B of this figure, there is no correlation between fecal excretion and clinical symptoms for strain BVF1. Fecal excretion of strain BVF1 reaches similar concentrations compared to excretion of strongly hemolytic *B. hyodysenteriae* strains but fecal scores of animals inoculated with strain BVF1 never exceed 1.

5. Plasma-Encoded Genes are Present in Strain BVF1

The three genes positioned around the origin of replication of the plasmid were present in all *B. hyodysenteriae* strains used in the different in vivo trials. Each strain was positive in PCR's using either one of the available primer pairs for each gene. The four plasmid based virulence associated genes were also present in all the different strains used for in vivo trials. Strain 8dII gave a positive result in PCR's using either one of the three available primer pairs for each gene, strains BVF1 and 49 gave a positive result using the primers: BHWA1_02678a-F/BHWA1_02678a-R, BHWA1_02679a-F/BHWA1_02679a-R and BHWA1_02679b-F/BHWA1_02679b-R, BHWA1_02680a-F/BHWA1_02680a-R and BHWA1_02680a-F/BHWA1_02680b-R, BHWA1_02681a-F/BHWA1_02681b-R and BHWA1_02681a-F/BHWA1_02681c-R.

It is herewith demonstrated that strain BVF1 is different from presently known avirulant strains, such as $B78^T$, SA2206, VS1, A1, B234, R301, B6933, and FM 88.90 (La et al., 2014) lacking all four plasmid based virulence associated genes.

Vaccinated Animals Show a Significantly Lower Fecal Score After Challenge with a Virulent *B. hyodysenteriae* Strain In the group of non-vaccinated animals 5 of 9 animals developed swine dysentery accompanied by the typical lesions on necropsy: fibronecrotic colitis with mucohaemorrhagic colonic content. In the vaccinated group 2 of 11 animals developed swine dysentery. Results are shown in table 7.

TABLE 7

Maximal fecal score, dysentery lesions on necropsy and presence of *B. hyodysenteriae* challenge strain B204 in the colon.

| | Non-vaccinated animals | | | Vaccinated animals | | |
|---|---|---|---|---|---|---|
| pig | Maximal fecal score[a] | Post mortem dysentery lesions | Presence of *B. hyodysenteriae* in the colon | pig | Maximal fecal score[a] | Post mortem dysentery lesions | Presence of *B. hyodysenteriae* in the colon |
| A | 2.5 m | yes | yes | 1 | 0 | no | no |
| B | 0 | no | no | 2 | 0 | no | no |
| C | 0 | no | no | 3 | 0 | no | no |
| D | 4 m, b | yes | yes | 5 | 4 m, b | yes | yes |
| E | 2.5 m | no | no | 6 | 4 m, b | yes | yes |
| F | 0 | no | no | 7 | 1 | no | no |
| G | 4 m, b | yes | yes | 8 | 1 | no | no |
| H | 4 m, b | yes | yes | 9 | 0 | no | no |
| I | 4 m, b | yes | yes | 10 | 0 | no | no |
| | | | | 11 | 0 | no | no |
| | | | | 12 | 0 | no | no |

[a]m = mucus present, b = blood present.

Figure 3:
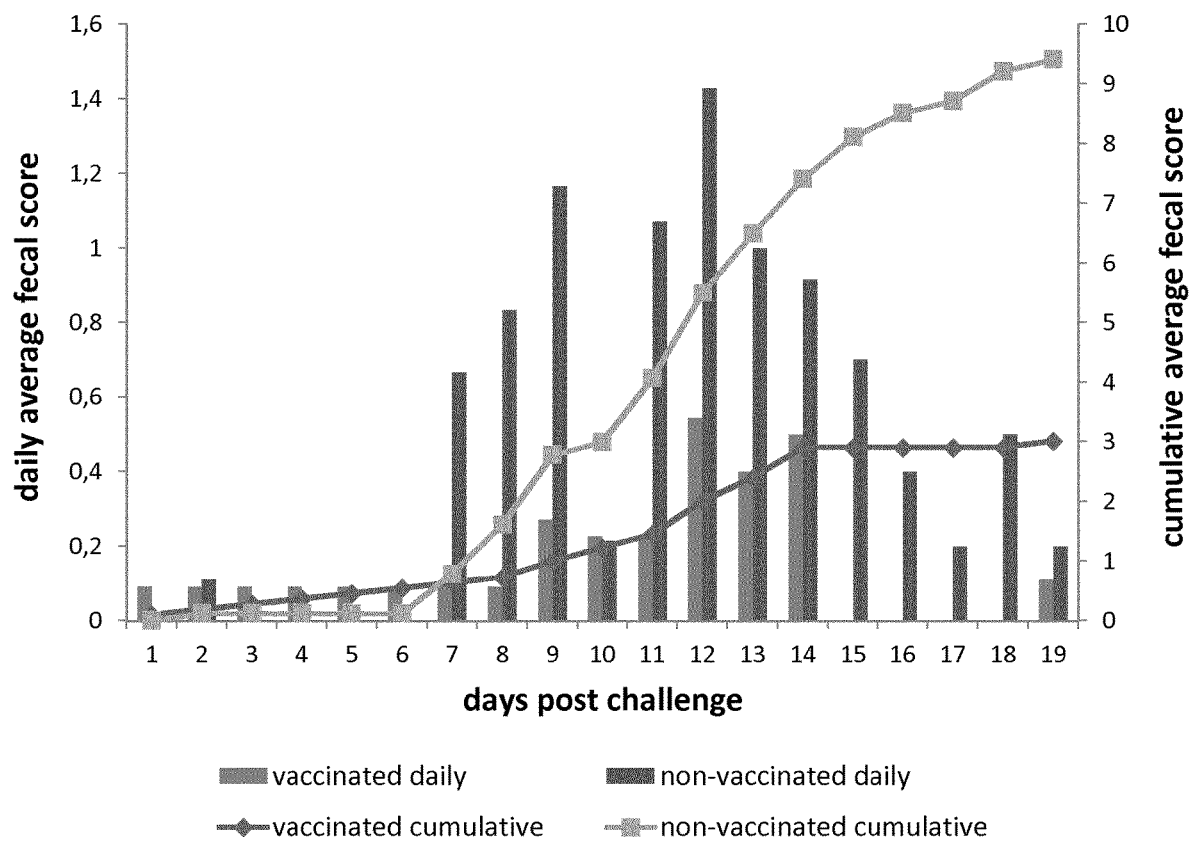
FIG. 3: Average fecal scores for vaccinated animals and non-vaccinated animals. Average fecal score for the vaccinated and non-vaccinated group. Left axis daily average in bars, right axis cumulative average in lines.

FIG. 3 shows the average fecal scores for the vaccinated group and the non-vaccinated group. Daily average fecal score (bars) as well as cumulative fecal score (lines) are given. The cumulative fecal score of the vaccinated group is significantly lower compared to the non-vaccinated group ($p<0.05$).

Vaccination Reduces Transmission of Swine Dysentery and Ameliorates Fecal Consistency In the groups of non-vaccinated animals seeder and receiver animals showed significantly higher fecal scores (=worse fecal consistency) compared to seeder and receiver animals in the vaccinated groups. This was demonstrated by the lower probability of vaccinated animals to obtain high fecal scores compared to non-vaccinated animals (ß=−1.67±0.43 s.e.). Furthermore it took significantly more time for vaccinated animals to develop higher fecal scores after contact with *B. hyodysenteriae* challenge strain B204 (ß=0.07±0.02 s.e.).

Figure 5:
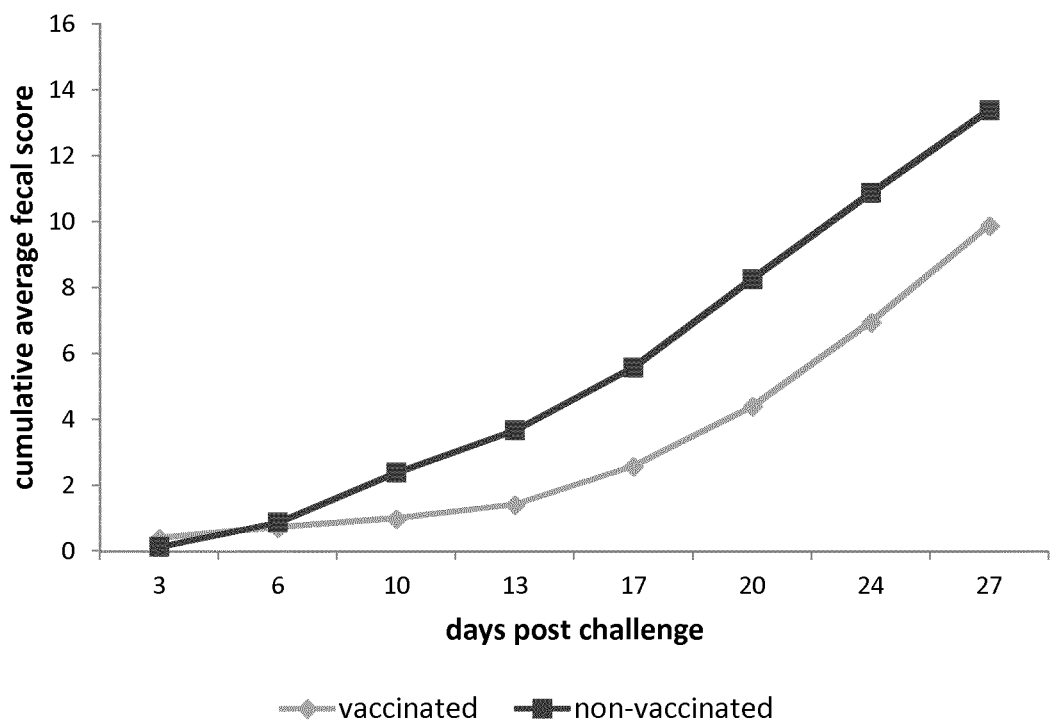
FIG. 5: cumulative average fecal scores for receiver animals in the vaccinated groups and the non-vaccinated groups.

FIG. 5 shows the cumulative average fecal scores for receiver animals in the vaccinated groups and the non-vaccinated groups.

In conclusion, the present invention provides a vaccine strain that is avirulent, capable of transiently colonizing pigs, and easily distinguishable from virulent field strains. It was demonstrated that after vaccination and subsequent challenge with a virulent *B. hyodysenteriae* strain, colonization and fecal shedding of the virulent strains is reduced, and clinical signs are less severe. Moreover, the vaccine strain reduces symptoms of dysentery without negative effects on growth and feed conversion related to natural infections.

The invention claimed is:

1. A method for treating diarrhea caused by *Brachyspira hyodysenteriae* in a pig in need thereof, the method comprising administering a therapeutically effective amount of a *Brachyspira hyodysenteriae* strain deposited on 23 Oct. 2015 at the Belgian Co-ordinated Collections of Micro-Organisms under BCCM Deposit No. LMG P-29184 to the pig.

2. The method of claim 1, wherein the diarrheal disease is swine dysentery.

3. The method of claim 1, wherein the strain is administered orally or parentally to the pig.

* * * * *

```
                              SEQUENCE LISTING

<160> NUMBER OF SEQ ID NOS: 45

<210> SEQ ID NO 1
<211> LENGTH: 1272
<212> TYPE: DNA
<213> ORGANISM: Brachyspira

<400> SEQUENCE: 1
atgcgtttag taagagaaaa aaaaataaaa gaagaggata aaaagtattg ggaaaaatca      60
agttctatga tacctaccct attagttggc aataacatag taaatatatc tgcgagttct     120
attataacag tatttgcagt aaggcttgct gatattctgc cgcatgtatc aacaaatata     180
atggttacaa tatcaactgc tacaataaca atacttatta ttatatttgg tgaaatactg     240
ccaaaagtct taatgagagt aaatgctgaa aaagtaatgc cttatctttt atactttatg     300
aaattttgcc attttatatt caagcctata acctttttaa tggataaagt aactactttt     360
ataatgaatt atttcgttcc taaaagatta agagatgctg aaaaaagaag tgcattatca     420
agtatggacg atataacaac aataatacat ttggggcata aagaaggtat aataaaagaa     480
tatacacatg aaatgcttac aggtgtaata gatttcagaa ataaaactgt agaagaaata     540
atgactcctc gtgttgatat ggtatgtatt gaggctgaaa ctgatgtaaa tgaaataata     600
aaacttactg tagaaacagg gctttcaaga tttccggttt atgaggaaac tgttgatcat     660
ataataggaa ttttccatac tagagcttta tttaaagagt atgttaaagg cggcggaaaa     720
atgaataaaa taaaaaagaa agcaatagat tatataatgc ttccctactt tgtacctgaa     780
actaaaacta taagcagctt atttagtgat atgcaaaaga aaaaacttca gatggtaatt     840
actattgatg aatacggcgg aactgctggg cttgttacta tggaagatat aatagaagag     900
ataatgggtg atatagaaga tgaaagtgat aaaaaagaag ctgatgtaat aagatttaag     960
ggaaaaagaa ttataataaa tggaaatgct tctatagaag atgtcaacaa aactttaaaa    1020
ttagaattag agcatgaaga atatcaaact atagcaggat atgttattga tatgcttgat    1080
catatacctg aaacaaatga gagattcata ttaaaaggat atagagtaag aataatgaaa    1140
gttgaagaca gaagaatagt tgaaatggaa tttactccta taaaatttgc aagaacaaat    1200
gaaagtgata atattgatat acaagagaca tctgattcag aaaaaaatga tttagaaatt    1260
ttaaatgaat aa                                                        1272

<210> SEQ ID NO 2
<211> LENGTH: 612
<212> TYPE: DNA
<213> ORGANISM: Brachyspira

<400> SEQUENCE: 2
atggagaaaa gtgcttttta tatagatata caaaacaaat ctaataaatc aaaaaagata      60
ggggagctat actcagcaat atcccatggc ataggagctt tacttggtat tgctggactt     120
gttcttatgc ttgtaaaaat aaaaatgaat cctataccta aattattta tggagttggt     180 ataatctttt tatatacatt cagttcttta tatcatttct ttcctgacgg taaaataaaa     240
caaatattta gaaaatttga tcacatagga atatatgtgt ttatagccgc aacttatact     300
ccagtttgta tattttcact tcctagaaac ataggaatac caatattatc agtaatatgg     360
```

| | |
|---|---|
| tcttgtgctt tgataggtat attatctaat acagttataa aatataaaaa tattgttcta | 420 |
| aggctagttt tatatatatt aatgggctgg ataataatat ttgcattcaa accattaatg | 480 |
| aatagatttg atattttgca tttaaattgg cttatatggg gaggaatatt ttatactata | 540 |
| ggtgctttct tatatgcttt aggtaaaaaa tgcaatgata aaactaagca attcactcat | 600 |
| gatattttcc at | 612 |

<210> SEQ ID NO 3
<211> LENGTH: 672
<212> TYPE: DNA
<213> ORGANISM: Brachyspira

<400> SEQUENCE: 3

| | |
|---|---|
| atgaatgctg atttgaataa taatatagta aagaattctg tttctaagat aagcgctgtt | 60 |
| atatgcataa tatgtgctag ttcggcaata gctgtcttag tgcttttaat aattaattct | 120 |
| aaaactgcaa gggaaattac ttcatttttct ctatactcaa gttttttaac aatattttat | 180 |
| ataataaatt cgatatatca ttttttttcct tttaacaata aagcaaaaaa agttttttat | 240 |
| atattatccc atgcattttt tattatgatg atatggggta tatacattcc tccatgccta | 300 |
| atatcattac aaaatggatg gggatggagt ttctttggta ttattacagg tttatgtgca | 360 |
| ttaggcatca cattaagaag cgtattcgga tacagatggc gtggtgctac agaaactata | 420 |
| tattattttc tattaaattg ggtttggctt atagcaattt caaaaatatc tactgctgta | 480 |
| ggtgaatatg gagcaatatt atatttaaca ggttttcttc tgctcaatat agcaatggta | 540 |
| ttttacagac tcgctatgta tgaagccaat agaagatata cttttatttt acctttattt | 600 |
| tattcgcttt taataatatc aaatatatgc catgcagtat ttatgtttag atatgttgct | 660 |
| aacattttct aa | 672 |

<210> SEQ ID NO 4
<211> LENGTH: 925
<212> TYPE: DNA
<213> ORGANISM: Brachyspira

<400> SEQUENCE: 4

| | |
|---|---|
| tatactgaaa cttttgaatc agtttatata acttcaaata tattagaaag caatcatact | 60 |
| caaatgcttt taaaagtaaa tatgagagat aaagaaagaa attctctttc tataataaaa | 120 |
| tctttccttg gattataata ctaatataaa tgcgattaga tgaatatgtg catagtgaat | 180 |
| gctatacaga aagcagatct aaagcacagg atataatact agccggttgt gttttttgtta | 240 |
| atggagtaaa ggtaacttct aaggctcata aaataaaaga tactgataat atagaagttg | 300 |
| ttcagaatat aaaatatgta tcaagagctg gagaaaaatt agaaaaggcg tttgtagaat | 360 |
| ttggaatatc tgtagaaaat aaaatatgtt tagatatagg agcttctaca ggaggattta | 420 |
| cagattgtct gcttaagcat ggtgctaaaa aagtttatgc tcttgatgta ggacataatc | 480 |
| agctagttta taacttcgt aatgataata gggtagtgtc aatagaagat ttcaatgcca | 540 |
| aagatataaa taaagaaatg ttcaatgatg aaatcccatc tgtaatagta agtgacgtat | 600 |
| catttatatc aataacaaaa atagcaccaa tcatatttaa agaattaaat aatttagagt | 660 |
| tttgggtaac tttaataaaa ccacaatttg aagctgaaag aggtgatgtt tcaaaaggcg | 720 |
| gtataatacg agatgatata cttagagaaa aaatattaaa taatgctatt tcaaagataa | 780 |
| tagactgcgg atttaaagaa gttaatgaaa ccatctctcc tataaaaggt gctaaaggta | 840 |
| atatagaata tttagctcat tttattattt aatcatttc tattttatgt gtatttctct | 900 |

```
gtttatatat ttcatattct ttata                                      925
```

<210> SEQ ID NO 5
<211> LENGTH: 2731
<212> TYPE: DNA
<213> ORGANISM: Brachyspira

<400> SEQUENCE: 5

```
taataaggac aattctcata agactaatac tgcatcatct agtaagacta acataaatgt    60
tgttaatgta gctaatagta gttttattta aaatttaaaa cctataatag aaattctaaa   120
ttatacatta gcattccttt atgttaatgt ataattttgt tttatttata atagtatttc   180
tattatatcc gataatgatt attaaaatat tttatatacg taaaatataa tacaggatta   240
taatatgttt caatttcatt taacaagcaa agcaaaaaag gtaatagaat tatatgctca   300
ggaagaagca aaaagattaa atcatgatat ggttacacct gaacatatac ttttggggct   360
tcttcatgaa tcagaggctt tggcaacacg tgttttgatg agattgaaaa ttgatttgga   420
cagacttaaa ttagaattag aatcagctat ggtaaaatct tcaactacaa agtatttgg    480
aactttacct acagctccaa gagtacagaa acttataagc agatctgctg aagaggctag   540
ggctttaagt cataactata taggtactga acatttactt cttggacttc taagagaaga   600
aagtggtaca gcttataatg tacttacaag tatggggctt gagcttacta tattaagaca   660
agaaatatta aaaatgcttg tgttgctgg aagtaatatt tcttctatgg aacagacaag   720
tcaggaagat aatgtaaaaa aggtaaaaac acctacttta gatcaatttg ccagagattt   780
aactaaaatg gctagagaca aggctttaga cagagttata ggcagagaaa atgaagtaat   840
gagagttgtt cagattttat caagaagaaa gaaaaataat cctatacttc ttggtgagcc   900
tggtgtaggt aaaacagcta tagtagaggg acttgctgaa aagatagtag ctgctgatgt   960
acctgatata cttctaaaaa aacgtgtatt aactttagat ttgtcttcag ttgttgctgg  1020
tacaaaatac agaggtgaat tgaagagag aataaaaaac atagttttag aaataaaaaa  1080
agctagtaat attattatat tcatagatga gcttcataca ttaatagggg caggtggtgc  1140
tgaaggtgct ttagatgctg ctaatatgtt aaagccggca ctttcaagag gcgagattca  1200
atgtataggt gccactacta taatgaata taaaaaatat atagaaaaag acggtgcttt  1260
ggttagaaga ttccagccta taaatgttga agagcctagt atagaggata ctattgaaat  1320
attgaatggt atcaaaggta aatatgaaga acatcataaa gtaaaatata ctgatgaagc  1380
aataaatgct gctactgtat tgagtaagag atatattttt gaaagacatt tgcctgataa  1440
agctatagac ttaatagatg aggcaggttc aagagcaaga cttcttaata tgacaagacc  1500
tcaggagttt aaagatttag aaaagaaaat agaaagctt aatcagcaaa agaaaagagt  1560
tgttgagagt cagaatttcg aagatgctgc taaaataaga gatgaaatta cttctttaca  1620
ggaagagctt tctaaaaaag aagaaaatg gcgtgaagaa agagaaaaga tagaaacatt  1680
tattgaagaa gatgatataa gacatgttat atcagaaata actaatatac ctataaaaag  1740
attattaaac tcagaaagta aaagacttat aggtatggaa gaagaattgc atcagaaagt  1800
cgtaggacag aaagaagcta tatcttctat atctaaggct ataagaagaa gcagagcagg  1860
acttaaaaca tcaaaaagac ctcttggaag ttttattttc ctgggaccta caggtgttgg  1920
taaaactgct ttagctaaag ttctttcaga gtttatgttt ggagacagcg atgctcttat  1980
cagaatagat atgagtgagt ttatggaaaa gtttgcggta agcagactta taggagctcc  2040
```

```
tcctggatat gttggttatg aagagggagg cggacttact gaaaaggtga aagaaaagcc    2100
ttattctctt atacttttg atgaaataga aaaagctcat cctgatgtta ctaatatact     2160
tttacaagta cttgaagaag gacagcttac tgataatttt ggaagaaaag ttgattttc     2220 aaatactatt ataataataa caagtaactt aggtgcaaga gatattgtaa aaggaagttc    2280
tttaggattt aatgctgttg gaagcgaaaa agatgctaat gatattaaaa attttgcttt    2340
agaagaatta aaacagaatt ttaatcctga gtttttaaat agaattgatg atatcatagt    2400
attccatact ttaagtaaag aggatttgaa agatattatt aatataatgc ttaaagagct    2460
taatgaagct attaaagaaa gaaatattgt tattaattta agcgaagaag ctaagaatta    2520
tatcatagat aaaggattcg ataagaagta tggtgctaga agtttaagaa gggctataca    2580
gaaagagata gaggattatg tgagtaccga aatattattc ggtaaaattg aagatggtga    2640
tactattaac gttgatgcta atgatggctc tttgatattt tcttatgata agtcagttaa    2700
gactgagaat aaggaattat ctaaaagtta g                                    2731
```

<210> SEQ ID NO 6
<211> LENGTH: 934
<212> TYPE: DNA
<213> ORGANISM: Brachyspira

<400> SEQUENCE: 6

```
taaaagggat acatcataat tatactagaa aatcattaat ggaaataat aagaaaatga     60 aggaattata caaaaagtg ataaaaacaa taaagaaaa taaatcataa tttaaggata     120
tatataaaat gccaataaaa aaattaatat ctaagatagt gaaaaaaaa gatagtgata    180 ctgaaaaaaa taattatata aatttatccg cattaacaga agcagaaaga gaaattataa    240
ctaatactat agaattgaaa tcaaagagcg taagagaaat aatggtgcct agggttgatg    300
ttgttatgat acctatggaa tcttcttatg ataaggttat aaaggctttt aatagagata    360
gaaattccag aattcctgta tacaaagacg gcatagatga tatagtaggg gttttgtatg    420
taaaagattt gattgatgca gaagaaaaaa atttctcact taaaaaaatt ctacataaac    480
ctttattcgt accaatatca atttcattaa tggaattatt aaaaaaattc agagaaaagc    540
aaattcatat tgctatggtt gttgatgaat atggcggatt ttctggtatt gtttctatgg    600
aagatgtgct tgagcagatt ataggtgata ttagagatga atacgatgaa gaagacgaag    660
aaataaagag caatgatgat ggaacatatt tagttgatgc aagaactaga atagatgatt    720
ttaataaata tgagatactt ccgcctatac cggatgatga ggcagataca gttggaggat    780
ttttattttc atacttgggc aggcttccta aaagaaatga ggatatagaa tataatggat    840
attcatttac tgtagttggt aaaagcggaa atattgttac taaataaga atagaaaat     900 taaaaaaaga taatacagca aaaaataaag atta                                934
```

<210> SEQ ID NO 7
<211> LENGTH: 468
<212> TYPE: DNA
<213> ORGANISM: Brachyspira

<400> SEQUENCE: 7

```
cggttgacgg cggaatgtca atgtaattat aaaaaagtat ataatgtgtt taaaaacact    60
ttattaataa acaatataca atttaaggag aattaaaaat ggcattaatc gatgaaatta    120
aagatgttgt tgctaatcaa ttaaacatct cagacaaaag taaatcacct gatacagctt    180
ctttcgtaga tgatttaaac gctgattcac ttgatttagt agaattaatc atggaattag    240
```

```
aaaaacgtta tgaaatcaaa attcctcaag aagatcaaga aaaaatcaaa aatgtagctg    300
atgctgctaa atacattgaa gaacataaaa aataattata ctatttaaat ttcccgtaaa    360
tagaattatg tcttttacgg gaaattttc gatatagttc aaaatcatag gagttttata    420
tatgagtgaa cgtagagttg taattacggg gcttggaata gtaagttc                468

<210> SEQ ID NO 8
<211> LENGTH: 1005
<212> TYPE: DNA
<213> ORGANISM: Brachyspira

<400> SEQUENCE: 8
ctatgctagt cctgaaagtt tgagaggtga aggcatcgat gtttatatgg gacatgatgt     60
tactaaaata gactgggcta acaaaaaatt atgtgtaaaa gaactaaaaa caggaaaaga    120
gtttgaagac acttacgata aacttattct tgctactggt tcttggcctg taactcctcc    180
tatcgaaggc ttaaaacaag aaggaactac ttacggactt aaaaaaggta ttttcttctc    240
taagctttat cagcaaggac aagaaattat tgatgaaata gctaaaccag atgttaaaaa    300
agttatggta gttggtgctg atacatagg tgttgaactt atagaagcat tcaaaaacca    360
tggtaaagaa gttatcttaa tggaagctat gcctagagtt atggctaact actttgataa    420
agaaatcact gatgaagctg aaaaaagaat caaagaagct ggcatagaaa tgcatttagg    480
tgaaactgtt aagaaatttg aaggtgatga cagagttaaa aaagttgtta ctgacaaagg    540
ttcttatgat gtagatatgg tagttatgtc tgttggtttc agacctaata atgaacttta    600
taaagattat ttagaaactt tacctaatgg tgctattgta gtagatacta ctatgaaaac    660
tactaaagat cctgatgtat ttgctatagg tgactgtgct actgtatatt caagagcttc    720
tgaaaaacaa gaatatattg cttttagctac taatgctgta agaatgggta ttgttgctgc    780
taataatgct ttaggaaaac atgttgaata ttgcggtact caaggttcta atgctatttg    840
tgtatttgga tacaatatgg cttctactgg ttggtctgaa gaaactgcta agaaaaaagg    900
attaaaagta aaatctaact tcttcaaaga ttctgaaaga ccagaattta tgcctactaa    960
tgaagatgtt ttagtaaaaa tcatttatga agaaggcagc agacg                  1005

<210> SEQ ID NO 9
<211> LENGTH: 1182
<212> TYPE: DNA
<213> ORGANISM: Brachyspira

<400> SEQUENCE: 9
cgcatatact cttgctacat aagtagagta gaggaaagga gcaatccgct ttacgatgag     60
cctgcggcct attagcctgt tggtgggta acggcctacc aaagctacga taggtagccg    120
acctgagagg gtgaccggcc acattgggac tgagatacgg cccagactcc tacgggaggc    180
agcagctgag aatcttccac aatggacgaa agtctgatgg agcgacatcg cgtgagggat    240
gaaggccttc gggttgtaaa cctcggaaat tatcgaagaa tgagtgacag tagataatgt    300
aagcctcggc taactacgtg ccagcagccg cggtaatacg taggaggcaa acgttgctcg    360
gatttactgg gcgtaaaggg tgagtaggcg gacttataag tctaaggtga agaccgaag    420 ctcaacttcg gaaacgcctc ggatactgta agtcttggat attgtagggg atgatggaat    480
tctcggtgta gcggtggaat gcgcagatat cgagaggaac acctatagcg aaggcagtca    540
tctgggcatt tatcgacgct gaatcacgaa agctagggga gcaaacaggc ttagataccc    600
```

```
tggtagtcct agccgtaaac gttgtacact aggtgcttct atttaaatag gagtgccgta    660
gctaacgtct taagtgtacc gcctgaggag tatgcccgca agggtgaaac tcaaagaaat    720
tgacgggtcc ccgcacaagt ggtggagcat gtggtttaat tcgatgatac gcgaaaaacc    780
ttacctgggg ttgaattgta agatgaatga tttagagata agtcagaccg caaggacgtt    840
ttacataggt gctgcatggc tgtcgtcagc tcgtgtcgtg agatgttggg ttaagtcccg    900
caacgagcgc aaccctcacc ctttgttgct accgagtaat gtcgggcact cttaggggac    960
tgcctacgtt caagtaggag gaaggtgggg atgatgtcaa gtcctcatgg cccttatgtc   1020
cagggctaca cacgtgctac aatggcaagt acaaagagaa gcaagaccgc gaggtggagc   1080
aaaactcaaa aaagttgcct cagttcggat tggagtctga aactcgactc catgaagttg   1140
gaatcactag taatcgtaga tcagaacgct acggtgaata cg                      1182
```

<210> SEQ ID NO 10
<211> LENGTH: 423
<212> TYPE: PRT
<213> ORGANISM: Brachyspira

<400> SEQUENCE: 10

```
Met Arg Leu Val Arg Glu Lys Lys Ile Lys Glu Glu Asp Lys Lys Tyr
1               5                   10                  15

Trp Glu Lys Ser Ser Ser Met Ile Pro Thr Leu Leu Val Gly Asn Asn
            20                  25                  30

Ile Val Asn Ile Ser Ala Ser Ser Ile Ile Thr Val Phe Ala Val Arg
        35                  40                  45

Leu Ala Asp Ile Leu Pro His Val Ser Thr Asn Ile Met Val Thr Ile
    50                  55                  60

Ser Thr Ala Thr Ile Thr Ile Leu Ile Ile Ile Phe Gly Glu Ile Leu
65                  70                  75                  80

Pro Lys Val Leu Met Arg Val Asn Ala Glu Lys Val Met Pro Tyr Leu
                85                  90                  95

Leu Tyr Phe Met Lys Phe Cys His Phe Ile Phe Lys Pro Ile Thr Phe
            100                 105                 110

Leu Met Asp Lys Val Thr Thr Phe Ile Met Asn Tyr Phe Val Pro Lys
        115                 120                 125

Arg Leu Arg Asp Ala Glu Lys Arg Ser Ala Leu Ser Ser Met Asp Asp
    130                 135                 140

Ile Thr Thr Ile Ile His Leu Gly His Lys Glu Gly Ile Ile Lys Glu
145                 150                 155                 160

Tyr Thr His Glu Met Leu Thr Gly Val Ile Asp Phe Arg Asn Lys Thr
                165                 170                 175

Val Glu Glu Ile Met Thr Pro Arg Val Asp Met Val Cys Ile Glu Ala
            180                 185                 190

Glu Thr Asp Val Asn Glu Ile Ile Lys Leu Thr Val Glu Thr Gly Leu
        195                 200                 205

Ser Arg Phe Pro Val Tyr Glu Glu Thr Val Asp His Ile Ile Gly Ile
    210                 215                 220

Phe His Thr Arg Ala Leu Phe Lys Glu Tyr Val Lys Gly Gly Gly Lys
225                 230                 235                 240

Met Asn Lys Ile Lys Lys Lys Ala Ile Asp Tyr Ile Met Leu Pro Tyr
                245                 250                 255

Phe Val Pro Glu Thr Lys Thr Ile Ser Ser Leu Phe Ser Asp Met Gln
            260                 265                 270
```

```
Lys Lys Lys Leu Gln Met Val Ile Thr Ile Asp Glu Tyr Gly Gly Thr
            275                 280                 285

Ala Gly Leu Val Thr Met Glu Asp Ile Ile Glu Ile Met Gly Asp
    290                 295                 300

Ile Glu Asp Glu Ser Asp Lys Lys Glu Ala Asp Val Ile Arg Phe Lys
305                 310                 315                 320

Gly Lys Arg Ile Ile Ile Asn Gly Asn Ala Ser Ile Glu Asp Val Asn
                325                 330                 335

Lys Thr Leu Lys Leu Glu Leu Glu His Glu Glu Tyr Gln Thr Ile Ala
                340                 345                 350

Gly Tyr Val Ile Asp Met Leu Asp His Ile Pro Glu Thr Asn Glu Arg
                355                 360                 365

Phe Ile Leu Lys Gly Tyr Arg Val Arg Ile Met Lys Val Glu Asp Arg
    370                 375                 380

Arg Ile Val Glu Met Glu Phe Thr Pro Ile Lys Phe Ala Arg Thr Asn
385                 390                 395                 400

Glu Ser Asp Asn Ile Asp Ile Gln Glu Thr Ser Asp Ser Glu Lys Asn
                405                 410                 415

Asp Leu Glu Ile Leu Asn Glu
                420

<210> SEQ ID NO 11
<211> LENGTH: 224
<212> TYPE: PRT
<213> ORGANISM: Brachyspira

<400> SEQUENCE: 11

Met Glu Lys Ser Ala Phe Tyr Ile Asp Ile Gln Asn Lys Ser Asn Lys
1               5                   10                  15

Ser Lys Lys Ile Gly Glu Leu Tyr Ser Ala Ile Ser His Gly Ile Gly
                20                  25                  30

Ala Leu Leu Gly Ile Ala Gly Leu Val Leu Met Leu Val Lys Ile Lys
            35                  40                  45

Met Asn Pro Ile Pro Ile Ile Tyr Gly Val Gly Ile Ile Phe Leu
    50                  55                  60

Tyr Thr Phe Ser Ser Leu Tyr His Phe Phe Pro Asp Gly Lys Ile Lys
65                  70                  75                  80

Gln Ile Phe Arg Lys Phe Asp His Ile Gly Ile Tyr Val Phe Ile Ala
                85                  90                  95

Ala Thr Tyr Thr Pro Val Cys Ile Phe Ser Leu Pro Arg Asn Ile Gly
                100                 105                 110

Ile Pro Ile Leu Ser Val Ile Trp Ser Cys Ala Leu Ile Gly Ile Leu
            115                 120                 125

Ser Asn Thr Val Ile Lys Tyr Lys Asn Ile Val Leu Arg Leu Val Leu
            130                 135                 140

Tyr Ile Leu Met Gly Trp Ile Ile Phe Ala Phe Lys Pro Leu Met
145                 150                 155                 160

Asn Arg Phe Asp Ile Leu His Leu Asn Trp Leu Ile Trp Gly Gly Ile
                165                 170                 175

Phe Tyr Thr Ile Gly Ala Phe Leu Tyr Ala Leu Gly Lys Lys Cys Asn
                180                 185                 190

Asp Lys Thr Lys Gln Phe Thr His Asp Ile Phe His Ile Phe Val Leu
            195                 200                 205

Met Gly Ser Phe Cys His Tyr Trp Phe Leu Tyr Ser Tyr Val Ile Asn
            210                 215                 220
```

<210> SEQ ID NO 12
<211> LENGTH: 223
<212> TYPE: PRT
<213> ORGANISM: Brachyspira

<400> SEQUENCE: 12

Met Asn Ala Asp Leu Asn Asn Ile Val Lys Asn Ser Val Ser Lys
1               5                   10                  15

Ile Ser Ala Val Ile Cys Ile Cys Ala Ser Ser Ala Ile Ala Val
                20                  25                  30

Leu Val Leu Leu Ile Ile Asn Ser Lys Thr Ala Arg Glu Ile Thr Ser
            35                  40                  45

Phe Ser Leu Tyr Ser Ser Phe Leu Thr Ile Phe Tyr Ile Ile Asn Ser
        50                  55                  60

Ile Tyr His Phe Phe Pro Phe Asn Asn Lys Ala Lys Lys Val Phe Tyr
65                  70                  75                  80

Ile Leu Ser His Ala Phe Phe Ile Met Met Ile Trp Gly Ile Tyr Ile
                85                  90                  95

Pro Pro Cys Leu Ile Ser Leu Gln Asn Gly Trp Gly Trp Ser Phe Phe
            100                 105                 110

Gly Ile Ile Thr Gly Leu Cys Ala Leu Gly Ile Thr Leu Arg Ser Val
        115                 120                 125

Phe Gly Tyr Arg Trp Arg Gly Ala Thr Glu Thr Ile Tyr Tyr Phe Leu
    130                 135                 140

Leu Asn Trp Val Trp Leu Ile Ala Ile Ser Lys Ile Ser Thr Ala Val
145                 150                 155                 160

Gly Glu Tyr Gly Ala Ile Leu Tyr Leu Thr Gly Phe Leu Leu Leu Asn
                165                 170                 175

Ile Ala Met Val Phe Tyr Arg Leu Ala Met Tyr Glu Ala Asn Arg Arg
            180                 185                 190

Tyr Thr Leu Phe Leu Pro Leu Phe Tyr Ser Leu Leu Ile Ile Ser Asn
        195                 200                 205

Ile Cys His Ala Val Phe Met Phe Arg Tyr Val Ala Asn Ile Phe
    210                 215                 220

<210> SEQ ID NO 13
<211> LENGTH: 240
<212> TYPE: PRT
<213> ORGANISM: Brachyspira

<400> SEQUENCE: 13

Met Arg Leu Asp Glu Tyr Val His Ser Glu Cys Tyr Thr Glu Ser Arg
1               5                   10                  15

Ser Lys Ala Gln Asp Ile Ile Leu Ala Gly Cys Val Phe Val Asn Gly
                20                  25                  30

Val Lys Val Thr Ser Lys Ala His Lys Ile Lys Asp Thr Asp Asn Ile
            35                  40                  45

Glu Val Val Gln Asn Ile Lys Tyr Val Ser Arg Ala Gly Glu Lys Leu
        50                  55                  60

Glu Lys Ala Phe Val Glu Phe Gly Ile Ser Val Glu Asn Lys Ile Cys
65                  70                  75                  80

Leu Asp Ile Gly Ala Ser Thr Gly Gly Phe Thr Asp Cys Leu Leu Lys
                85                  90                  95

His Gly Ala Lys Lys Val Tyr Ala Leu Asp Val Gly His Asn Gln Leu
            100                 105                 110

```
Val Tyr Lys Leu Arg Asn Asp Asn Arg Val Val Ser Ile Glu Asp Phe
            115                 120                 125

Asn Ala Lys Asp Ile Asn Lys Glu Met Phe Asn Asp Glu Ile Pro Ser
130                 135                 140

Val Ile Val Ser Asp Val Ser Phe Ile Ser Ile Thr Lys Ile Ala Pro
145                 150                 155                 160

Ile Ile Phe Lys Glu Leu Asn Asn Leu Glu Phe Trp Val Thr Leu Ile
                165                 170                 175

Lys Pro Gln Phe Glu Ala Glu Arg Gly Asp Val Ser Lys Gly Gly Ile
            180                 185                 190

Ile Arg Asp Asp Ile Leu Arg Glu Lys Ile Leu Asn Asn Ala Ile Ser
            195                 200                 205

Lys Ile Ile Asp Cys Gly Phe Lys Glu Val Asn Arg Thr Ile Ser Pro
210                 215                 220

Ile Lys Gly Ala Lys Gly Asn Ile Glu Tyr Leu Ala His Phe Ile Ile
225                 230                 235                 240
```

<210> SEQ ID NO 14
<211> LENGTH: 828
<212> TYPE: PRT
<213> ORGANISM: Brachyspira

<400> SEQUENCE: 14

```
Met Phe Gln Phe His Leu Thr Ser Lys Ala Lys Lys Val Ile Glu Leu
1               5                   10                  15

Tyr Ala Gln Glu Glu Ala Lys Arg Leu Asn His Asp Met Val Thr Pro
            20                  25                  30

Glu His Ile Leu Leu Gly Leu Leu His Glu Ser Glu Ala Leu Ala Thr
        35                  40                  45

Arg Val Leu Met Arg Leu Lys Ile Asp Leu Asp Arg Leu Lys Leu Glu
50                  55                  60

Leu Glu Ser Ala Met Val Lys Ser Thr Thr Lys Val Phe Gly Thr
65                  70                  75                  80

Leu Pro Thr Ala Pro Arg Val Gln Lys Leu Ile Ser Arg Ser Ala Glu
                85                  90                  95

Glu Ala Arg Ala Leu Ser His Asn Tyr Ile Gly Thr Glu His Leu Leu
            100                 105                 110

Leu Gly Leu Leu Arg Glu Glu Ser Gly Thr Ala Tyr Asn Val Leu Thr
        115                 120                 125

Ser Met Gly Leu Glu Leu Thr Ile Leu Arg Gln Glu Ile Leu Lys Met
130                 135                 140

Leu Gly Val Ala Gly Ser Asn Ile Ser Ser Met Glu Gln Thr Ser Gln
145                 150                 155                 160

Glu Asp Asn Val Lys Lys Val Lys Thr Pro Thr Leu Asp Gln Phe Ala
                165                 170                 175

Arg Asp Leu Thr Lys Met Ala Arg Asp Lys Ala Leu Asp Arg Val Ile
            180                 185                 190

Gly Arg Glu Asn Glu Val Met Arg Val Gln Ile Leu Ser Arg Arg
            195                 200                 205

Lys Lys Asn Asn Pro Ile Leu Leu Gly Glu Pro Gly Val Gly Lys Thr
210                 215                 220

Ala Ile Val Glu Gly Leu Ala Glu Lys Ile Val Ala Ala Asp Val Pro
225                 230                 235                 240

Asp Ile Leu Leu Lys Lys Arg Val Leu Thr Leu Asp Leu Ser Ser Val
```

```
                245                 250                 255
Val Ala Gly Thr Lys Tyr Arg Gly Glu Phe Glu Glu Arg Ile Lys Asn
            260                 265                 270
Ile Val Leu Glu Ile Lys Lys Ala Ser Asn Ile Ile Phe Ile Asp
        275                 280                 285
Glu Leu His Thr Leu Ile Gly Ala Gly Ala Gly Ala Leu Asp
    290                 295                 300
Ala Ala Asn Met Leu Lys Pro Ala Leu Ser Arg Gly Glu Ile Gln Cys
305                 310                 315                 320
Ile Gly Ala Thr Thr Ile Asn Glu Tyr Lys Lys Tyr Ile Glu Lys Asp
                325                 330                 335
Gly Ala Leu Val Arg Arg Phe Gln Pro Ile Asn Val Glu Glu Pro Ser
            340                 345                 350
Ile Glu Asp Thr Ile Glu Ile Leu Asn Gly Ile Lys Gly Lys Tyr Glu
        355                 360                 365
Glu His His Lys Val Lys Tyr Thr Asp Glu Ala Ile Asn Ala Ala Thr
    370                 375                 380
Val Leu Ser Lys Arg Tyr Ile Phe Glu Arg His Leu Pro Asp Lys Ala
385                 390                 395                 400
Ile Asp Leu Ile Asp Glu Ala Gly Ser Arg Ala Arg Leu Leu Asn Met
                405                 410                 415
Thr Arg Pro Gln Glu Phe Lys Asp Leu Glu Lys Lys Ile Glu Glu Leu
            420                 425                 430
Asn Gln Gln Lys Lys Arg Val Val Glu Ser Gln Asn Phe Glu Asp Ala
        435                 440                 445
Ala Lys Ile Arg Asp Glu Ile Thr Ser Leu Gln Glu Glu Leu Ser Lys
    450                 455                 460
Lys Glu Glu Lys Trp Arg Glu Glu Arg Glu Lys Ile Glu Thr Phe Ile
465                 470                 475                 480
Glu Glu Asp Asp Ile Arg His Val Ile Ser Glu Ile Thr Asn Ile Pro
                485                 490                 495
Ile Lys Arg Leu Leu Asn Ser Glu Ser Lys Arg Leu Ile Gly Met Glu
            500                 505                 510
Glu Glu Leu His Gln Lys Val Val Gly Gln Lys Glu Ala Ile Ser Ser
        515                 520                 525
Ile Ser Lys Ala Ile Arg Arg Ser Arg Ala Gly Leu Lys Thr Ser Lys
    530                 535                 540
Arg Pro Leu Gly Ser Phe Ile Phe Leu Gly Pro Thr Gly Val Gly Lys
545                 550                 555                 560
Thr Ala Leu Ala Lys Val Leu Ser Glu Phe Met Phe Gly Asp Ser Asp
                565                 570                 575
Ala Leu Ile Arg Ile Asp Met Ser Glu Phe Met Glu Lys Phe Ala Val
            580                 585                 590
Ser Arg Leu Ile Gly Ala Pro Pro Gly Tyr Val Gly Tyr Glu Glu Gly
        595                 600                 605
Gly Gly Leu Thr Glu Lys Val Arg Arg Lys Pro Tyr Ser Leu Ile Leu
    610                 615                 620
Phe Asp Glu Ile Glu Lys Ala His Pro Asp Val Thr Asn Ile Leu Leu
625                 630                 635                 640
Gln Val Leu Glu Glu Gly Gln Leu Thr Asp Asn Phe Gly Arg Lys Val
                645                 650                 655
Asp Phe Ser Asn Thr Ile Ile Ile Thr Ser Asn Leu Gly Ala Arg
            660                 665                 670
```

-continued

Asp Ile Val Lys Gly Ser Ser Leu Gly Phe Asn Ala Val Gly Ser Glu
            675                 680                 685

Lys Asp Ala Asn Asp Ile Lys Asn Phe Ala Leu Glu Glu Leu Lys Gln
690                 695                 700

Asn Phe Asn Pro Glu Phe Leu Asn Arg Ile Asp Asp Ile Ile Val Phe
705                 710                 715                 720

His Thr Leu Ser Lys Glu Asp Leu Lys Asp Ile Ile Asn Ile Met Leu
            725                 730                 735

Lys Glu Leu Asn Glu Ala Ile Lys Glu Arg Asn Ile Val Ile Asn Leu
            740                 745                 750

Ser Glu Glu Ala Lys Asn Tyr Ile Ile Asp Lys Gly Phe Asp Lys Lys
            755                 760                 765

Tyr Gly Ala Arg Ser Leu Arg Arg Ala Ile Gln Lys Glu Ile Glu Asp
            770                 775                 780

Tyr Val Ser Thr Glu Ile Leu Phe Gly Asn Ile Glu Asp Gly Asp Thr
785                 790                 795                 800

Ile Asn Val Asp Ala Asn Asp Gly Ser Leu Ile Phe Ser Tyr Asp Lys
            805                 810                 815

Ser Val Lys Thr Glu Asn Lys Glu Leu Ser Lys Ser
            820                 825

<210> SEQ ID NO 15
<211> LENGTH: 268
<212> TYPE: PRT
<213> ORGANISM: Brachyspira

<400> SEQUENCE: 15

Met Pro Ile Lys Lys Leu Ile Ser Lys Ile Val Lys Lys Asp Ser
1               5                   10                  15

Asp Thr Glu Lys Asn Asn Tyr Ile Asn Leu Ser Ala Leu Thr Glu Ala
            20                  25                  30

Glu Arg Glu Ile Ile Thr Asn Thr Ile Glu Leu Lys Ser Lys Ser Val
            35                  40                  45

Arg Glu Ile Met Val Pro Arg Val Asp Val Val Met Ile Pro Met Glu
50                  55                  60

Ser Ser Tyr Asp Lys Val Ile Lys Ala Phe Asn Arg Asp Arg Asn Ser
65                  70                  75                  80

Arg Ile Pro Val Tyr Lys Asp Gly Ile Asp Ile Val Gly Val Leu
            85                  90                  95

Tyr Val Lys Asp Leu Ile Asp Ala Glu Glu Lys Asn Phe Ser Leu Lys
            100                 105                 110

Lys Ile Leu His Lys Pro Leu Phe Val Pro Ile Ser Ile Ser Leu Met
            115                 120                 125

Glu Leu Leu Lys Asn Phe Arg Glu Lys Gln Ile His Ile Ala Met Val
            130                 135                 140

Val Asp Glu Tyr Gly Gly Phe Ser Gly Ile Val Ser Met Glu Asp Val
145                 150                 155                 160

Leu Glu Gln Ile Ile Gly Asp Ile Arg Asp Glu Tyr Asp Glu Asp
            165                 170                 175

Glu Glu Ile Lys Ser Asn Asp Asp Gly Thr Tyr Leu Val Asp Ala Arg
            180                 185                 190

Thr Arg Ile Asp Asp Phe Asn Lys Tyr Glu Ile Leu Pro Pro Ile Pro
            195                 200                 205

Asp Asp Glu Ala Asp Thr Val Gly Gly Phe Leu Phe Ser Tyr Leu Gly

```
            210                 215                 220
Arg Leu Pro Lys Arg Asn Glu Asp Ile Glu Tyr Asn Gly Tyr Ser Phe
225                 230                 235                 240

Thr Val Val Gly Lys Ser Gly Asn Ile Val Thr Lys Ile Arg Ile Glu
                245                 250                 255

Lys Leu Lys Lys Asp Asn Thr Ala Lys Asn Lys Asp
            260                 265
```

<210> SEQ ID NO 16
<211> LENGTH: 78
<212> TYPE: PRT
<213> ORGANISM: Brachyspira

<400> SEQUENCE: 16

```
Met Ala Leu Ile Asp Glu Ile Lys Asp Val Ala Asn Gln Leu Asn
1               5                   10                  15

Ile Ser Asp Lys Ser Lys Ile Thr Asp Thr Ala Ser Phe Val Asp Asp
                20                  25                  30

Leu Asn Ala Asp Ser Leu Asp Leu Val Glu Leu Ile Met Glu Leu Glu
            35                  40                  45

Lys Arg Tyr Glu Ile Lys Ile Pro Gln Glu Asp Gln Glu Lys Ile Lys
50                  55                  60

Asn Val Ala Asp Ala Ala Lys Tyr Ile Glu Glu His Lys Lys
65                  70                  75
```

<210> SEQ ID NO 17
<211> LENGTH: 335
<212> TYPE: PRT
<213> ORGANISM: Brachyspira

<400> SEQUENCE: 17

```
Tyr Ala Ser Pro Glu Ser Leu Arg Gly Glu Gly Ile Asp Val Tyr Met
1               5                   10                  15

Gly His Asp Val Thr Lys Ile Asp Trp Ala Asn Lys Lys Leu Cys Val
                20                  25                  30

Lys Glu Leu Lys Thr Gly Lys Glu Phe Glu Asp Thr Tyr Asp Lys Leu
            35                  40                  45

Ile Leu Ala Thr Gly Ser Trp Pro Val Thr Pro Ile Glu Gly Leu
50                  55                  60

Lys Gln Glu Gly Thr Thr Tyr Gly Leu Lys Lys Gly Ile Phe Phe Ser
65                  70                  75                  80

Lys Leu Tyr Gln Gln Gly Gln Glu Ile Ile Asp Glu Ile Ala Lys Pro
                85                  90                  95

Asp Val Lys Lys Val Met Val Gly Ala Gly Tyr Ile Gly Val Glu
            100                 105                 110

Leu Ile Glu Ala Phe Lys Asn His Gly Lys Glu Val Ile Leu Met Glu
        115                 120                 125

Ala Met Pro Arg Val Met Ala Asn Tyr Phe Asp Lys Glu Ile Thr Asp
    130                 135                 140

Glu Ala Glu Lys Arg Ile Lys Glu Ala Gly Ile Glu Met His Leu Gly
145                 150                 155                 160

Glu Thr Val Lys Lys Phe Glu Gly Asp Asp Arg Val Lys Lys Val Val
                165                 170                 175

Thr Asp Lys Gly Ser Tyr Asp Val Asp Met Val Val Met Ser Val Gly
            180                 185                 190

Phe Arg Pro Asn Asn Glu Leu Tyr Lys Asp Tyr Leu Glu Thr Leu Pro
```

```
            195                 200                 205
Asn Gly Ala Ile Val Asp Thr Thr Met Lys Thr Thr Lys Asp Pro
    210                 215                 220

Asp Val Phe Ala Ile Gly Asp Cys Ala Thr Val Tyr Ser Arg Ala Ser
225                 230                 235                 240

Glu Lys Gln Glu Tyr Ile Ala Leu Ala Thr Asn Ala Val Arg Met Gly
                245                 250                 255

Ile Val Ala Ala Asn Asn Ala Leu Gly Lys His Val Glu Tyr Cys Gly
            260                 265                 270

Thr Gln Gly Ser Asn Ala Ile Cys Val Phe Gly Tyr Asn Met Ala Ser
        275                 280                 285

Thr Gly Trp Ser Glu Glu Thr Ala Lys Lys Gly Leu Lys Val Lys
    290                 295                 300

Ser Asn Phe Phe Lys Asp Ser Glu Arg Pro Glu Phe Met Pro Thr Asn
305                 310                 315                 320

Glu Asp Val Leu Val Lys Ile Ile Tyr Glu Glu Gly Ser Arg Arg
                325                 330                 335

<210> SEQ ID NO 18
<211> LENGTH: 25
<212> TYPE: DNA
<213> ORGANISM: Brachyspira

<400> SEQUENCE: 18
gtttgatyct ggctcagarc kaacg                                              25

<210> SEQ ID NO 19
<211> LENGTH: 25
<212> TYPE: DNA
<213> ORGANISM: Brachyspira

<400> SEQUENCE: 19
cttccggtac ggmtgccttg ttacg                                              25

<210> SEQ ID NO 20
<211> LENGTH: 21
<212> TYPE: DNA
<213> ORGANISM: Brachyspira

<400> SEQUENCE: 20
tagcytgcgg tatygcwctt t                                                  21

<210> SEQ ID NO 21
<211> LENGTH: 22
<212> TYPE: DNA
<213> ORGANISM: Brachyspira

<400> SEQUENCE: 21
gcmtgwatag cttcrgcatg rt                                                 22

<210> SEQ ID NO 22
<211> LENGTH: 20
<212> TYPE: DNA
<213> ORGANISM: Brachyspira

<400> SEQUENCE: 22
ggtattggag atgaatatac                                                    20

<210> SEQ ID NO 23
<211> LENGTH: 20
```

```
<212> TYPE: DNA
<213> ORGANISM: Brachyspira

<400> SEQUENCE: 23
tgatgtagaa ggcttctata                                              20

<210> SEQ ID NO 24
<211> LENGTH: 20
<212> TYPE: DNA
<213> ORGANISM: Brachyspira

<400> SEQUENCE: 24
ggagtggaga gaaagtatta                                              20

<210> SEQ ID NO 25
<211> LENGTH: 20
<212> TYPE: DNA
<213> ORGANISM: Brachyspira

<400> SEQUENCE: 25
tgctgtaagc agacttatag                                              20

<210> SEQ ID NO 26
<211> LENGTH: 20
<212> TYPE: DNA
<213> ORGANISM: Brachyspira

<400> SEQUENCE: 26
agctgtcctt cttcaagtac                                              20

<210> SEQ ID NO 27
<211> LENGTH: 20
<212> TYPE: DNA
<213> ORGANISM: Brachyspira

<400> SEQUENCE: 27
agtcgtagga cagaaagaag                                              20

<210> SEQ ID NO 28
<211> LENGTH: 20
<212> TYPE: DNA
<213> ORGANISM: Brachyspira

<400> SEQUENCE: 28
ccctcttcat aaccaacata                                              20

<210> SEQ ID NO 29
<211> LENGTH: 20
<212> TYPE: DNA
<213> ORGANISM: Brachyspira

<400> SEQUENCE: 29
agggacttgc tgaaaagata                                              20

<210> SEQ ID NO 30
<211> LENGTH: 20
<212> TYPE: DNA
<213> ORGANISM: Brachyspira

<400> SEQUENCE: 30
ttgtaccagc aacaactgaa                                              20

<210> SEQ ID NO 31
```

```
<211> LENGTH: 20
<212> TYPE: DNA
<213> ORGANISM: Brachyspira

<400> SEQUENCE: 31
agctctatct acagcaatac                                               20

<210> SEQ ID NO 32
<211> LENGTH: 20
<212> TYPE: DNA
<213> ORGANISM: Brachyspira

<400> SEQUENCE: 32
ttacgaatgc ctgctatttg                                               20

<210> SEQ ID NO 33
<211> LENGTH: 20
<212> TYPE: DNA
<213> ORGANISM: Brachyspira

<400> SEQUENCE: 33 ctattttag gcgaggcttt                                                20

<210> SEQ ID NO 34
<211> LENGTH: 20
<212> TYPE: DNA
<213> ORGANISM: Brachyspira

<400> SEQUENCE: 34
ggaaaaaggg atcctggaac                                               20

<210> SEQ ID NO 35
<211> LENGTH: 20
<212> TYPE: DNA
<213> ORGANISM: Brachyspira

<400> SEQUENCE: 35
tcctgcttgt tatcagcaca                                               20

<210> SEQ ID NO 36
<211> LENGTH: 20
<212> TYPE: DNA
<213> ORGANISM: Brachyspira

<400> SEQUENCE: 36
ctattggaga gcgtacatct                                               20

<210> SEQ ID NO 37
<211> LENGTH: 20
<212> TYPE: DNA
<213> ORGANISM: Brachyspira

<400> SEQUENCE: 37
taccctgtac ctacagaaca                                               20

<210> SEQ ID NO 38
<211> LENGTH: 20
<212> TYPE: DNA
<213> ORGANISM: Brachyspira

<400> SEQUENCE: 38
ctcctcccgt tcaatatgta                                               20
```

-continued

```
<210> SEQ ID NO 39
<211> LENGTH: 20
<212> TYPE: DNA
<213> ORGANISM: Brachyspira

<400> SEQUENCE: 39
aatccgccat gtaaaactgc                                                  20

<210> SEQ ID NO 40
<211> LENGTH: 18
<212> TYPE: DNA
<213> ORGANISM: Brachyspira

<400> SEQUENCE: 40
tggtgaaata ctgccaaa                                                    18

<210> SEQ ID NO 41
<211> LENGTH: 20
<212> TYPE: DNA
<213> ORGANISM: Brachyspira

<400> SEQUENCE: 41
tgttgttata tcgtccatac                                                  20

<210> SEQ ID NO 42
<211> LENGTH: 21
<212> TYPE: DNA
<213> ORGANISM: Brachyspira

<400> SEQUENCE: 42
gttaatgctg aaaaaatgat g                                                21

<210> SEQ ID NO 43
<211> LENGTH: 21
<212> TYPE: DNA
<213> ORGANISM: Brachyspira

<400> SEQUENCE: 43
aagctcttgt atggaatata c                                                21

<210> SEQ ID NO 44
<211> LENGTH: 19
<212> TYPE: DNA
<213> ORGANISM: Brachyspira

<400> SEQUENCE: 44
caagttctat gatacctac                                                   19

<210> SEQ ID NO 45
<211> LENGTH: 21
<212> TYPE: DNA
<213> ORGANISM: Brachyspira

<400> SEQUENCE: 45
gccgccttta acataytctt t                                                21
```